US012364867B2

(12) United States Patent
Nobles et al.

(10) Patent No.: US 12,364,867 B2
(45) Date of Patent: Jul. 22, 2025

(54) SYSTEM AND METHOD FOR OPERATING AN IMPLANTABLE PULSE GENERATOR FOR NEUROMODULATION

(71) Applicant: ADVANCED NEUROMODULATION SYSTEMS, INC., Plano, TX (US)

(72) Inventors: Robert Nobles, Frisco, TX (US); Greg Creek, Prosper, TX (US); Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 821 days.

(21) Appl. No.: 17/501,741

(22) Filed: Oct. 14, 2021

(65) Prior Publication Data

US 2022/0203107 A1 Jun. 30, 2022

Related U.S. Application Data

(60) Provisional application No. 63/132,028, filed on Dec. 30, 2020.

(51) Int. Cl.
*A61N 1/372* (2006.01)
*A61N 1/36* (2006.01)
*A61N 1/378* (2006.01)

(52) U.S. Cl.
CPC ..... *A61N 1/37247* (2013.01); *A61N 1/36125* (2013.01); *A61N 1/36157* (2013.01); *A61N 1/36175* (2013.01); *A61N 1/37252* (2013.01); *A61N 1/37264* (2013.01); *A61N 1/378* (2013.01)

(58) Field of Classification Search
CPC ............ A61N 1/37247; A61N 1/36125; A61N 1/36157; A61N 1/36175; A61N 1/37252; A61N 1/37264; A61N 1/378; A61N 1/36071
See application file for complete search history.

(56) References Cited

U.S. PATENT DOCUMENTS

| 5,335,657 A | 8/1994 | Terry et al. |
| 6,622,047 B2 | 9/2003 | Barrett et al. |

(Continued)

*Primary Examiner* — Eugene T Wu
(74) *Attorney, Agent, or Firm* — Norton Rose Fulbright US LLP

(57) ABSTRACT

A system and method for operating an implanted medical device (IMD) based on a waveform player. In one arrangement, the IMD may comprise a first module operative to effectuate a communication interface with an external device for receiving a plurality of program records for storage in a persistent memory, the program records each comprising a plurality of pulse definitions and a plurality of time interval definitions, wherein a pulse definition comprises a set of pulse characteristics to be applied in a particular time interval. A second module may be communicatively coupled to the first module, the second module including a buffer for containing a runtime image of a selected program record loaded from the persistent memory. A waveform player provided as part of the second module is operative to interpret the runtime image to generate control signals to drive an output driver circuit for applying pulse characteristics to a select set of electrodes according to the pulse definitions of the selected program record.

7 Claims, 12 Drawing Sheets

(56) References Cited

U.S. PATENT DOCUMENTS

| | | | |
|---|---|---|---|
| 6,721,603 B2 | 4/2004 | Zabara et al. | |
| 7,024,246 B2 | 4/2006 | Acosta et al. | |
| 7,715,912 B2 | 5/2010 | Rezai et al. | |
| 8,082,033 B2 | 12/2011 | Rezai et al. | |
| 9,008,790 B2 | 4/2015 | Griffith et al. | |
| 9,144,687 B2 | 9/2015 | Griffith et al. | |
| 9,288,614 B1 | 3/2016 | Young et al. | |
| 9,474,905 B2 | 10/2016 | Doan et al. | |
| 2008/0208284 A1* | 8/2008 | Rezai | A61B 5/369 607/45 |
| 2014/0364920 A1* | 12/2014 | Doan | A61N 1/37247 607/46 |
| 2018/0304083 A1 | 10/2018 | De Ridder | |
| 2019/0160294 A1* | 5/2019 | Peterson | A61N 1/36064 |

* cited by examiner

| 15 | 14 | 13 | 12 | 11 | 10 | 9 | 8 | 7 | 6 | 5 | 4 | 3 | 2 | 1 | 0 |
|----|----|----|----|----|----|---|---|---|---|---|---|---|---|---|---|
| HEADER ||||||||||||||||
| FORMAT VERSION 1004 |||||||| RECORD TYPE 1006 ||||||||
| LXD | ~X~ | ~X~ | ~X~ | ~X~ | ~X~ | ~X~ | ~X~ | OD | LD | ~X~ | STCLKF |||| MA |
| NUMBER OF PULSES ||||||||||||||||
| NUMBER OF INTERVALS ||||||||||||||||
| SCRATCH BYTES ||||||||||||||||
| DOSE ON TIME(S) {ZERO FOR NON-STOP} ||||||||||||||||
| DOSE ON TIME(S) {ZERO FOR A SINGLE BOLUS} ||||||||||||||||
| STIMULATION SHUTOFF DELAY ||||||||||||||||

| 15 | 14 | 13 | 12 | 11 | 10 | 9 | 8 | 7 | 6 | 5 | 4 | 3 | 2 | 1 | 0 |
|----|----|----|----|----|----|---|---|---|---|---|---|---|---|---|---|
| PULSE ||||||||||||||||
| TargetAmplitude 1032 |||||||| MaxAmplitude 1034 ||||||||
| I-RANGE 1036 |||||||| PulseWidth 1038 ||||||||
| SLOPE INTEGER (M) |||||||| SLOPE FRACTION (N) ||||||||
| DISCHARGE |||| CAN |||| VMO | PWE | PDF | ~X~ | ~X~ | ~X~ | ~X~ | ~X~ |
| MOST REPRESENTATIVE INTERVAL INDEX ||||||||||||||||
| ELECTRODES(0) |||||||| ELECTRODES(1) ||||||||
| ELECTRODES(2) |||||||| ELECTRODES(3) ||||||||

| 15 | 14 | 13 | 12 | 11 | 10 | 9 | 8 | 7 | 6 | 5 | 4 | 3 | 2 | 1 | 0 |
|----|----|----|----|----|----|---|---|---|---|---|---|---|---|---|---|
| INTERVAL ||||||||||||||||
| TIME TO NEXT PULSE(INTERVAL) ||||||||||||||||
| PULSE INDEX 1054 |||||||| OPE | ODE | PWE | PDF | ~X~ | ~X~ | ~X~ | ~X~ |
| VMULT 1058 |||||||| ADC 1060 ||||||||
| RepeatCnt 1062 |||||||| NUMBER OF RECORDS TO REPEAT 1064 ||||||||

SYSTEM AND METHOD FOR OPERATING AN IMPLANTABLE PULSE GENERATOR FOR NEUROMODULATION

PRIORITY AND CROSS-REFERENCE TO RELATED APPLICATION(S)

This nonprovisional application claims priority based upon the following prior United States provisional patent application(s): (i) "SYSTEM AND METHOD FOR OPERATING AN IMPLANTABLE PULSE GENERATOR FOR NEUROMODULATION," Application No.: 63/132,028, filed Dec. 30, 2020, in the name(s) of Robert Nobles et al., each of which is hereby incorporated by reference in its entirety.

TECHNICAL FIELD

This application is generally related to neuromodulation and, in some embodiments, to a system and method for operating an implantable pulse generator for neuromodulation using a waveform player.

BACKGROUND

Implantable medical devices (IMDs) have changed how medical care is provided to patients having a variety of chronic illnesses and disorders. For example, implantable cardiac devices improve cardiac function in patients with heart disease by improving quality of life and reducing mortality rates. Respective types of implantable neurostimulators or pulse generators provide a reduction in pain for chronic pain patients and reduce motor difficulties in patients with Parkinson's disease and other movement disorders. A variety of other medical devices are proposed and are in development to treat other disorders in a wide range of patients.

IMDs are programmed by and transmit data to external devices controlled by physicians, the patient, and/or their respective agents. The external devices communicate by forming wireless bi-directional communication links with the IMDs. For example, an external device of the patient (e.g., patient's programmer) may only be configured to form a wireless bi-directional communication link with the IMD implanted in the patient. However, the external device of the clinician (e.g., doctor, nurse) may be configured to form wireless bi-directional communication links with multiple IMDs.

Recently, there has been a growing trend for the external devices to communicate using Bluetooth, WiFi, or other commercial protocols compatible with commercial wireless devices such as tablet computers, smartphones, and the like (commonly referred to as commercial off-the-shelf (COTS) equipment).

Whereas advances in IMD systems and associated stimulation methodologies for use in various therapy applications continue to take place at a steady pace, several lacunae remain, thereby requiring further innovation as will be set forth hereinbelow.

SUMMARY

Example embodiments of the present patent disclosure are directed to systems, methods and associated computer-readable media for operating an implanted medical device (IMD) or implantable pulse generator (IPG) for providing neuromodulation using a waveform player. In one aspect, an embodiment of an IMD may comprise a first module operative to effectuate a communication interface with an external device for receiving a plurality of program records for storage in a persistent memory, the program records each comprising a plurality of pulse definitions and a plurality of time interval definitions, wherein a pulse definition comprises a set of pulse characteristics to be applied in a particular time interval. A second module may be communicatively coupled to the first module, the second module including a buffer for containing a runtime image of a selected program record loaded from the persistent memory. A waveform player provided as part of the second module is operative to interpret the runtime image to generate control signals to drive an output driver circuit for applying pulse characteristics to a select set of electrodes according to the pulse definitions of the selected program record.

In one arrangement, the set of pulse characteristics defined in a pulse definition of a selected program record may comprise at least one of a target amplitude, a maximum amplitude, a current range, a pulse width, a discharge method, one or more indicia identifying the select set of electrodes, one or more indicia identifying whether a particular one of the select set of electrodes is operative as a cathode or an anode, and a time interval index operative to associate a time interval definition therewith. In one arrangement, a program record may comprise a header including an indicator identifying a number of pulses, an indicator identifying a number of time intervals, and a record type indicator indicating whether the program record is a therapy record for applying a stimulation therapy to the patient or a diagnostic record for performing a runtime impedance measurement with respect to the select set of electrodes. In one arrangement, the header of a program record may further comprise an indicator for identifying whether the program record is to be executed in a loop over a predetermined time period. In one arrangement, a time interval definition of a program record may comprise a configurable time duration and a pulse index indicator identifying a specific pulse definition to be applied for the time duration. In one arrangement, the output driver circuit associated with a waveform player of the present patent disclosure may comprise a two-way set associative cache of 8 sets of registers for associatively mapping 16 pulse definitions to stimulate up to 16 electrodes of an example IMD's lead system. In one arrangement, the buffer for containing the runtime image of a selected program record may comprise a double-buffered memory.

In another aspect, an embodiment of a stimulation therapy method using an IMD is disclosed, wherein the IMD includes a power supply and a lead system of one or more leads having a plurality of electrodes positioned proximate to a tissue of a patient. The claimed embodiment may comprise, inter alia, obtaining a plurality of program records from an external device, each program record including a plurality of pulse definitions and a plurality of time interval definitions, wherein a pulse definition comprises a set of pulse characteristics to be applied in a particular time interval; loading a runtime image of a particular program record into an active program buffer; and interpreting the runtime image to generate control signals to drive an output driver circuit for applying pulse characteristics to a select set of electrodes according to the pulse definitions of the particular program record. In one arrangement, the method may comprise executing the program record until termination. In another arrangement, the method may comprise continuing to generate the control signals to drive the output driver circuit according to the particular program record in a loop mode.

In yet another aspect, a therapy system including an external device and an IMD having a waveform player as set forth herein is disclosed wherein a stimulation therapy according to a select program record may be applied to a patient. In one arrangement, the external device may comprise a clinician programmer device, a patient controller device or a delegated agent device operative on behalf a clinician or a patient. Depending on a deployment scenario, the external device may be provided as a COTS device or a non-COTS device. In one arrangement, the stimulation therapy applied by the selected program record may comprise a therapy selected from at least one of a spinal cord or column stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

In still further aspects, one or more embodiments of a non-transitory computer-readable medium or distributed media containing computer-executable program instructions or code portions stored thereon are disclosed for performing example methods herein when executed by a processor entity of a patient controller device, a clinician programmer device, a delegated agent device, an IMD, etc. that may be modified appropriately, mutatis mutandis.

Additional/alternative features and variations of the embodiments as well as the advantages thereof will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 10A-10C depict additional details relative to different portions of an example program record according to an embodiment of the present patent disclosure;

DETAILED DESCRIPTION

Figure 1:
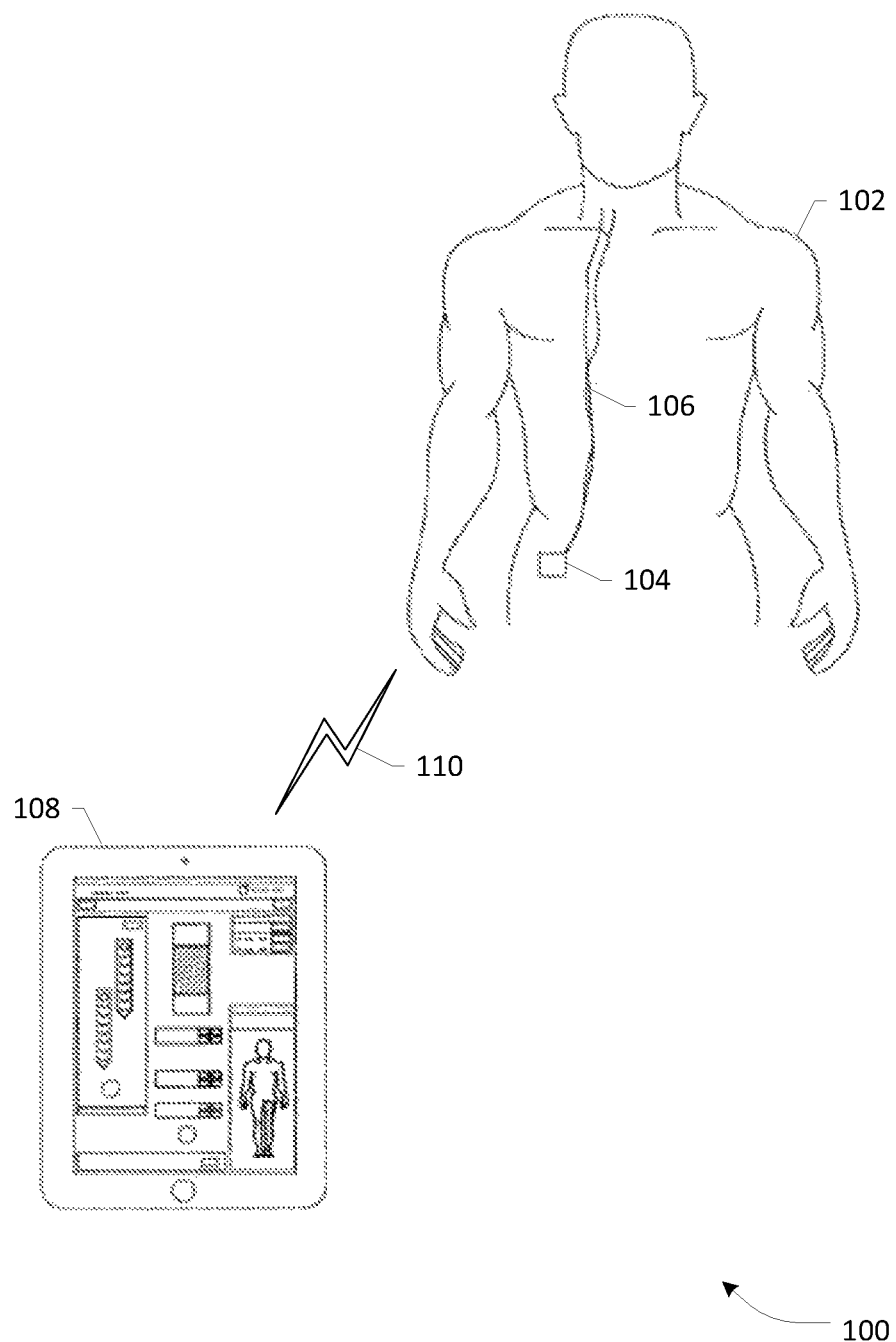
FIG. 1 depicts an example therapy system wherein an implantable medical device (IMD) and associated external device (ED) may be configured to provide stimulation therapy to a patient using waveform generation according to one or more embodiments of the present patent disclosure.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some example embodiments described herein may relate to operating an IPG based on waveform generation and playback for providing therapy to a desired area of a body or tissue in response to a suitable stimulation therapy application hosted by an external device, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, drug delivery systems, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example modules, circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1, depicted therein is an example therapy system wherein an implantable medical device (IMD) and associated external device may be configured to provide stimulation therapy to a patient using waveform generation according to one or more embodiments of the present patent disclosure. Example therapy system 100 is illustrative of a patient 102 having an IMD 104 and an external device 108 that may be controlled by the patient 102 and/or an authorized healthcare provider, e.g., a medical professional or technician, and/or an authorized agent respectively thereof having appropriate level(s) of privilege authorization, to administer different aspects relative to providing therapy to the patient 102 by communicating with IMD 104. External device 108 may comprise commercial off-the-shelf (COTS) equipment such as a portable computer, smartphone, tablet, phablet, laptop, or the like, or a proprietary portable medical/healthcare device, which may be configured to execute a therapy application program or "app", wherein various types of communications relating to control, therapy/diagnostics, and/or device file management including the generation of stimulation therapy program records or "waveforms" and the transmission thereof to a suitable storage in IMD 104 may be effectuated between one or more modules of external device 108 and IMD 104 for administering therapy as will be set forth in detail further below. Example IMD 104 may be implanted within the patient 102, e.g., proximate to the spinal cord or other tissue or organ depending on the therapy, wherein one or more leads 106 having one or more electrodes and/or sensors (not specifically shown in this FIG.) may be activated or energized pursuant to a select waveform or stimulation program record to provide therapy and/or obtain sensory/diagnostic information. Additionally or alternatively, IMD 104 may have components that are external to the patient 102; for example, IMD 104 may be associated with an external pulse generator (EPG) or other non-invasive personal medical device that may also be configured to provide therapy and/or obtain therapy data.

In one arrangement, external device 108 may be configured to establish a local wireless telemetry communication link, e.g., a bi-directional communication link 110, with IMD 104 for facilitating a therapy application executing on external device 108 to, inter alia, receive various pieces of information, e.g., therapy measurements, sensory data, personal data, logging data, etc., from IMD 104, and to program or send instructions to IMD 104, using a standard or proprietary communication protocol stack on the external device that may also be commonly accessible to one or more other applications or software programs hosted by the external device 108. In one arrangement, the bi-directional communication link 110 may be effectuated via a wireless personal area network (WPAN) using a standard wireless protocol such as Bluetooth Low Energy (BLE), Bluetooth, Wireless USB, Zigbee, Near-Field Communications (NFC), WiFi, Infrared Wireless, and the like. In some arrangements, communication link 110 may also be established using magnetic induction techniques rather than radio waves, e.g., via an induction wireless mechanism. Alternatively and/or additionally, communication link 110 may be effectuated in accordance with certain healthcare-specific communications services including, Medical Implant Communication Service (MICS), Wireless Medical Telemetry Service (WMTS), Medical Device Radiocommunications Service (MDRS), Medical Data Service (MDS), etc. Accordingly, regardless of which type(s) of communication technology being used, external device 108 and IMD 104 may each be provided with appropriate hardware, software and firmware (e.g., forming suitable communication circuitry including transceiver circuitry and antenna circuitry where necessary) for effectuating communication link 110, along with corresponding protocol stacks executing on respective device platforms. In some implementations, therefore, wireless telemetry communications between external device 108 and IMD 104 may be effectuated as M2M communications based on appropriate protocols. Furthermore, external device 108 and IMD 104 may each be provisioned with suitable security credential information that may be used for facilitating an application-specific authentication scheme and/or a device authentication scheme as an overlay layer based on provisioning.

Figure 2:
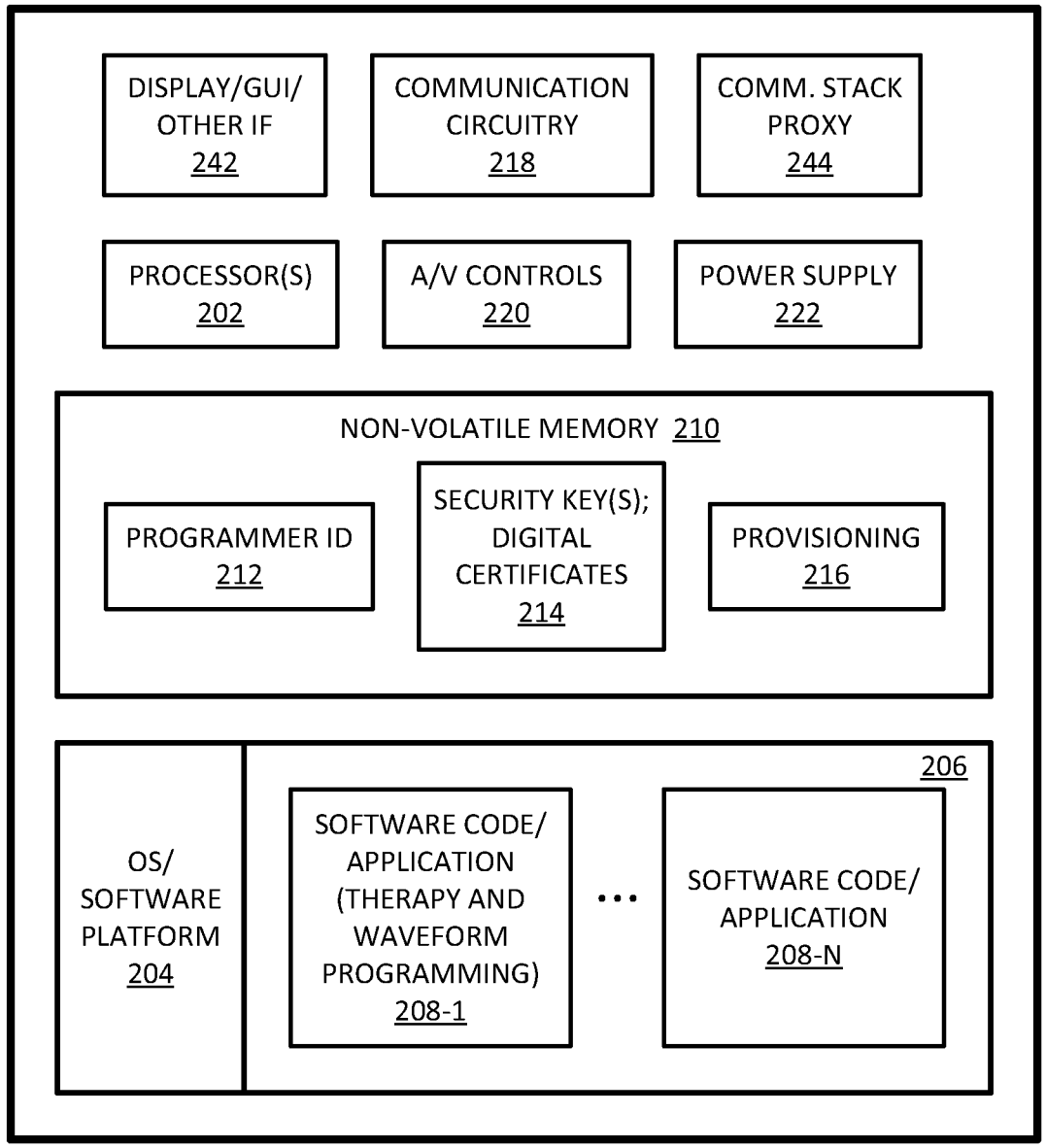
FIG. 2 depicts a block diagram of an external device according to an example embodiment of the present patent disclosure.

FIG. 2 depicts a block diagram of an external device 200 according to an example embodiment of the present patent disclosure. Depending on configuration and/or modality, external device 200 may be representative of a patient controller device, a clinician programmer device, or a delegated device operated by an agent of a patient or a clinician having subordinate levels of privilege authorization with respect to a therapy application (e.g., role setting), which may include suitable program code for generating therapy program records, each containing a plurality of pulse definitions, time interval definitions, inter alia, for transmission to and storage at an IMD as will be seen further below. Further, external device 200 may be a COTS device or non-COTS device as previously noted. Still further, external device 200 may be a device that is controlled and managed in a centralized enterprise device management system (EDMS), also referred to as a mobile/medical device management system (MDMS), which may be associated with the manufacturer of the device and associated therapy application components in some embodiments (either as an intranet implementation, an extranet implementation, or internet-based cloud implementation, etc.), in order to ensure that only appropriately managed devices and users are allowed to engage in providing therapy to patients using approved therapy applications. Still further, external device 200 may be a device that is not controlled and managed in such a device management system. Accordingly, it will be realized that external device 200 may be a device that may be configured in a variety of ways depending on how its functional modality is implemented in a particular deployment.

Example external device 200 may include one or more processors 202, communication circuitry 218 and one or more memory modules 210, operative in association with one or more OS platforms 204 and one or more software applications 208-1 to 208-K depending on configuration, cumulatively referred to as device software environment 206, and any other hardware/software/firmware modules, all being powered by a power supply 222, e.g., battery. Example software environment 206 and/or memory 210 may include one or more persistent memory modules comprising program code or instructions for controlling overall operations of the device, inter alia. Example OS platforms may include embedded real-time OS systems, and may be selected from, without limitation, iOS, Android, Chrome OS, Blackberry OS, Ubuntu, Sailfish OS, Windows, Kai OS, eCos, LynxOS, QNX, RTLinux, Symbian OS, VxWorks, Windows CE, MontaVista Linux, SafeRTOS, FreeRTOS, and the like. In some embodiments, at least a portion of the software applications may include code or program instructions operative as a therapy application, e.g., application 208-1, which may be configured to interoperate with program code stored in memory 210 to execute various operations relative to device registration, waveform programming, security applications, and provisioning as part of a device controller application. Further, application 208-1 may include code or program instructions configured to effectuate wireless telemetry and authentication with an IMD using a suitable communication protocol stack, e.g., stack 244, in association with a communication proxy under processor control.

Memory modules 210 may include a non-volatile storage area or module configured to store relevant patient data, therapy settings, and the like. Memory modules 210 may further include a secure storage area 212 to store a device identifier (e.g., a serial number) of device 200 used during programming sessions (e.g., local programming or remote session programming). Also, memory modules 210 may include a secure storage area 214 for storing security credential information, e.g., one or more cryptographic keys or key pairs, signed digital certificates, etc., associated with users (e.g., clinicians, patients, or respective agents), certificates of trusted entities, which may be operative in association with approved software applications, e.g., therapy application 208-1, that may be obtained during provisioning. Communication circuitry 218 may include appropriate hardware, software and interfaces to facilitate wireless and/or wireline communications, e.g., inductive communications, wireless telemetry or M2M communications, etc. to effectuate IMD communications, as well as networked communications with cellular telephony networks, local area networks (LANs), wide area networks (WANs), packet-switched data networks, etc., based on a variety of access technologies and communication protocols. External device 200 may also include appropriate audio/video controls 220 as well as suitable display(s) (e.g., touch screen), camera(s), microphone, and other user interfaces (1.11s) 242, which may be utilized for purposes of some example embodiments of the present disclosure, e.g., facilitating user input, initiating IMD communications, therapy modulation, etc.

Figure 3:
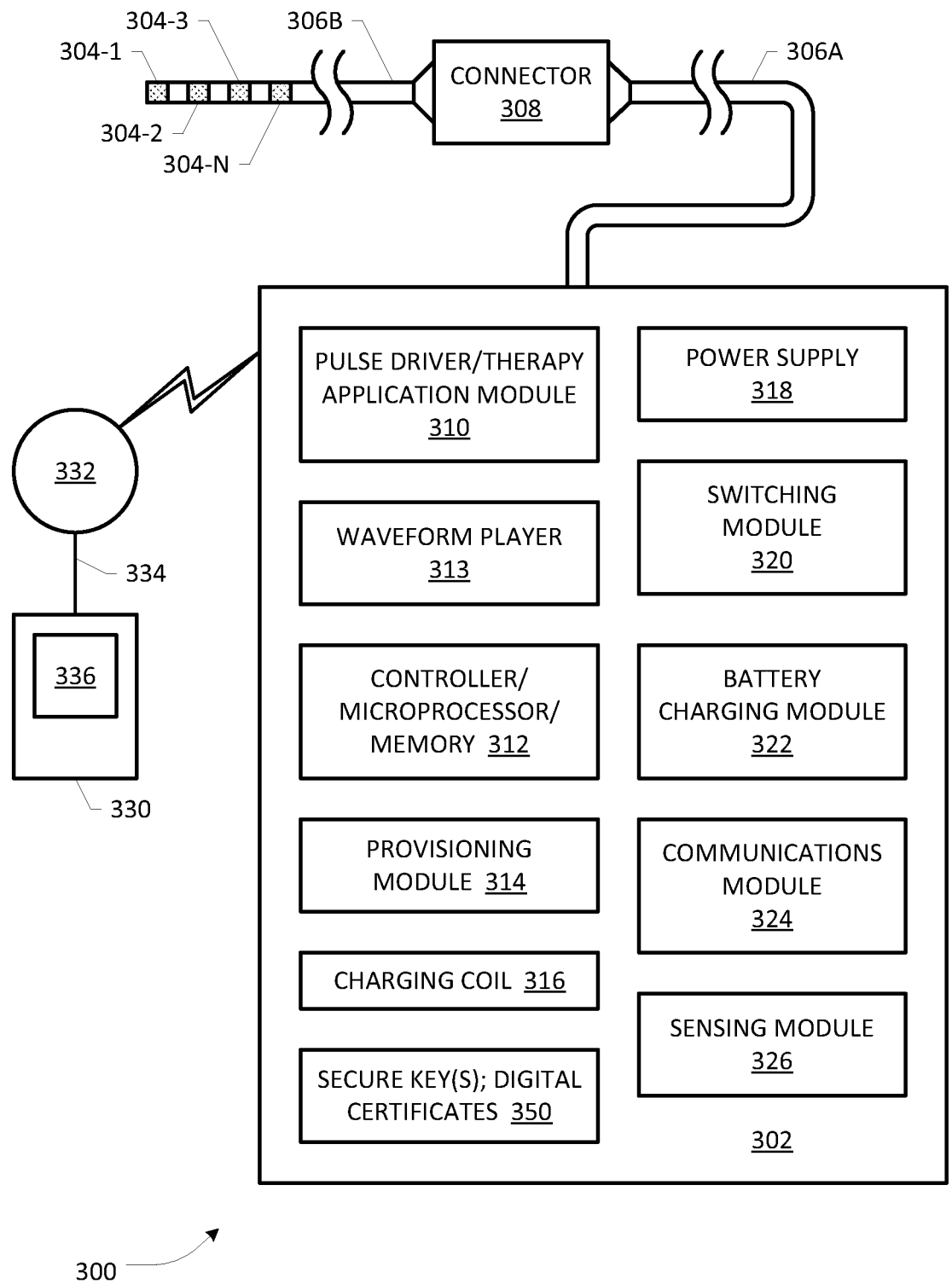
FIG. 3 depicts a block diagram of an IMD and associated system that may be configured for providing therapy using waveform generation according to an example embodiment of the present patent disclosure.

FIG. 3 depicts a block diagram of an IMD and associated system that may be configured for providing therapy based on stored waveforms or stimulation program records according to an example embodiment of the present patent disclosure. By way of illustration, system 300 may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as previously noted. System 300 includes an IMD 302, also referred to as an embedded device in some embodiments, that is adapted to generate stimulation pulses according to a selected program record containing a plurality of pulse definitions, a plurality of interval definitions, etc. (also referred to a playback of the program record). In one example embodiment, IMD 302 may be implemented as having a metallic housing or can that encloses controller/processing and embedded memory modules 312, pulse driving circuitry with therapy application module 310 including or operative with a waveform player 313, a charging coil 316, a battery or power source 318, a far-field and/or near field communication block or module 324 operative with applicable communication protocol stacks (not specifically shown), battery charging circuitry 322, switching circuitry 320, sensing circuitry 326, and the like. Controller/processor module 312 may include one or more microcontrollers or other suitable processors for controlling the various other components of IMD 302, e.g., with respect to communications and control operations. In some embodiments, separate processors may be provided for managing communications with external devices, including obtaining and storing waveforms, and controlling pulse generation based on a select waveform program (e.g., effectuating a programmable stimulation engine or "stim" engine). Accordingly, the IMD's software/firmware code (e.g., RTOS) may be stored in memory 312 of IMD 302 and/or may also be separately provided and/or integrated with other suitable application-specific integrated circuits and/or storage components (not specifically shown in this FIG.) for execution by the microcontroller(s) or processor(s) 312 and/or other programmable logic blocks to control the various components of the device for purposes of an embodiment of the present patent disclosure.

In one arrangement, IMD 302 may be coupled to a lead system having a lead connector 308 for coupling a first component 306A emanating from IMD 302 with a second component 306B that includes a plurality of electrodes 304-1 to 304-N, which may be positioned proximate to the patient tissue. Although a single lead system 306A/306B is exemplified, it should be appreciated that an example lead system may include more than one lead, each having a respective number of electrodes for providing therapy according to a program record selected for playback by waveform player 313 in association with pulse generation and output driver circuitry 310 operating as a stimulation engine. In one arrangement, an example program record downloaded into a buffer, e.g., associated with processor circuitry 312 and/or module 310, may include different combinations of multiple pulse definitions and time interval definitions operative to provide various combinations of lead/electrode selection settings, one or more sets of stimulation parameters corresponding to different lead/electrode combinations, respectively, such as pulse amplitude, pulse width or duty cycle, pulse frequency or inter-pulse period, pulse repetition parameter, etc. In one arrangement, pulse definition parameters and interval definition parameters may be selectively varied and combined to provide stimulation in myriad ways that can be identified as e.g., tonic stimulation, burst stimulation, noise stimulation, biphasic stimulation, monophasic stimulation, or any stimulation pattern having irregularities intentionally designed therein, and/or the like, as will be set forth further below. Additionally, a program record may include electrode configuration data for delivery of electrical pulses (e.g., as cathodic nodes, anodic nodes, or configured as inactive nodes, etc.), e.g., on a pulse-by-pulse basis, stimulation pattern identification etc. Still further, therapy programming data may be accompanied with respective metadata, which may include data that identifies the physician or clinician that created or programmed the settings data. In some embodiments, the metadata may include an identifier of the external programmer device that was used to create the settings data, the date of creation, the data of last modification, the physical location where programming occurred, and/or any other relevant data or indicia.

In still further arrangements, a program record may include an identifier or indicia operative to indicate or otherwise instruct waveform player 313 as to the type or category to which the program record belongs, which may specify a particular sequence of programmed pulse definitions and time interval definitions or a default sequence, as will be seen further below.

In some embodiments, IMD 302 may include a secure storage area 350 for storing security credential information such as, e.g., one or more cryptographic keys or key pairs, signed digital certificates, etc., associated with the device and/or approved software applications, e.g., therapy application 310, that may be obtained during provisioning. Accordingly, in some embodiments, a provisioning module 314 may be provided for obtaining security credential information during the manufacture of the device using the manufacturer's established root of trust system with a known public key infrastructure (PKI) system. In some embodiments, IMD 302 may be manufactured in an unprovisioned state, which may be configured to obtain security credential information via a third-party trusted entity, e.g., a medical entity, that relies on its own root of trust supplied under a PKI system. Regardless of the exact manner of provisioning as to how IMD 302 obtains security credential information and/or the type of communication channel it has with an authorized external device, it will be seen below that a plurality of waveforms or programs may be downloaded or transmitted as files to the IMD for storage thereat and/or a waveform may be generated on the fly at the external device that may be transmitted dynamically to the IMD for playback in real time.

As noted previously, example external device 330 may be deployed for use with IMD 302 for therapy application including waveform generation and transmission, management and monitoring purposes, e.g., as a patient controller device or a clinician programmer device, upon establishing appropriate communication channels. Generally, external device 330 may be implemented to charge/recharge the battery 318 of IPG/IMD 302 (although a separate recharging device could alternatively be employed), to access memory 312 and/or any secure file systems thereof containing patient/program data, and/or to program or reprogram IMD 302 with respect to one or more waveforms including pulse definitions and time interval definitions while implanted within the patient. In alternative embodiments, however, separate programmer devices may be employed for charging and/or programming the IMD device 302 device and/or any programmable components thereof. Software stored within a non-transitory memory of the external device 330 may be executed by a processor to control the various operations of the external device 330, including executing a therapy application adapted to operate with IMD 302. Depending on the type of communication technology used, a connector or "wand" 334 may be electrically coupled to the external device 330 in some arrangements using suitable electrical connectors (not specifically shown), which may be electrically connected to a telemetry component 332 (e.g., inductor coil, RF transceiver, etc.) at the distal end of wand 334 through respective communication links that allow bi-directional communication with IMD 302. Alternatively, there may be no separate or additional external communication/telemetry components provided with example external device 330 in an example embodiment for facilitating bi-directional communications with IMD 302 (e.g., based on BLE).

In one arrangement, a user (e.g., a doctor, a medical technician, or the patient) may initiate communication with IMD 302 by placing wand 334 proximate to the patient's body containing the IMD. Preferably, the placement of the wand 334 allows the telemetry system to be aligned with the communication circuitry 324 of IMD 302. External device 330 preferably includes one or more user interfaces 336 (e.g., touch screen, keyboard, mouse, buttons, scroll wheels or rollers, or the like), allowing the user to operate IMD 302. External device 330 may be controlled by the user through interface 336, allowing the user to interact with IMD 302, whereby operations involving waveform programming, diagnostic monitoring (e.g., electrode impedance monitoring) etc. may be effectuated pursuant to executing different modules of a therapy application that has been authenticated according to some example embodiments.

Figure 4:
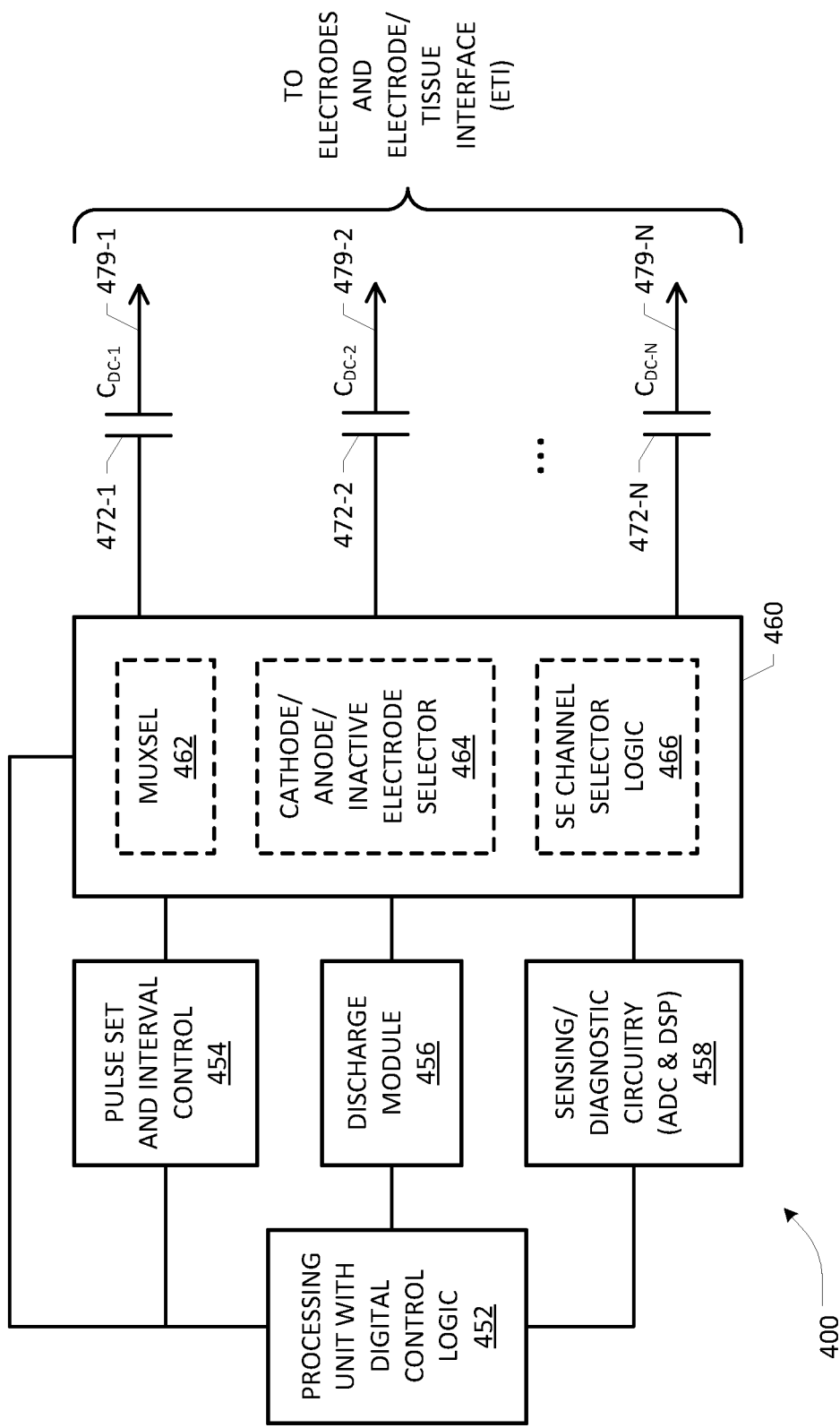
FIG. 4 depicts a block diagram of a programmable stimulation engine portion having waveform generation control and associated lead electrode arrangement according to an embodiment of the present patent disclosure.
Figure 5:
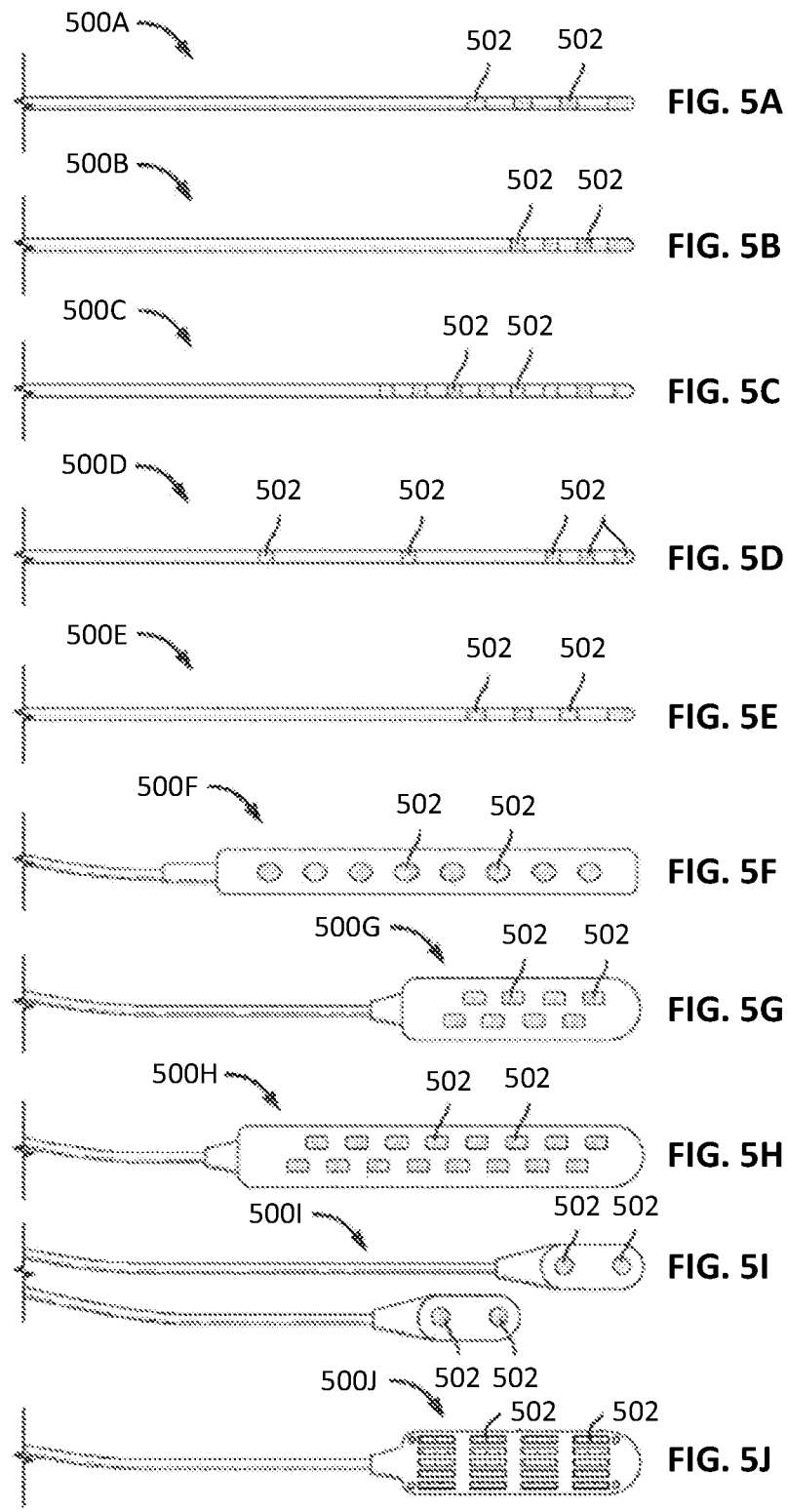
FIGS. 5A-5J illustrate example electrical stimulation leads that may be energized using waveform generation according to an embodiment of the present patent disclosure.

FIG. 4 depicts a block diagram of a programmable stimulation engine portion 400 having waveform generation control and associated lead electrode arrangement according to an embodiment of the present patent disclosure. One skilled in the art will recognize upon reference hereto that various functionalities associated with example blocks shown as part of the stimulation engine portion 400 may be distributed and/or integrated among one or more blocks, subsystems and/or modules described hereinabove with respect to IMD 302 of FIG. 3 and/or other drawing Figures set forth herein. Consistent with the description provided elsewhere in the present patent disclosure, an example processing unit 452 having or associated with suitable digital control logic and waveform player functionality is operatively coupled to pulse/timing definition control 454, discharge module 456 (e.g., for effectuating/controlling either passive or active discharge modes with respect to energized electrodes) and sensing/diagnostic circuitry 458 for facilitating various functionalities including but not limited to voltage measurements, impedance measurements, active discharge cycling or charge balancing, electrode selection and configuration, as well as stimulation engine (SE) selection where multiple SEs are provided, etc. under appropriate programmatic/diagnostics control. An input/output (I/O) driver interface block 460 is operatively coupled to a plurality of lead connectors 479-1 to 479-N interfaced with respective electrodes, which interfaces may be modeled as suitable lumped-element electrode/tissue interface (ETI) loads or circuit representations, wherein the lead connectors and associated electrodes may be configured as one or more leads, each having a respective plurality of electrodes. Regardless of the number of leads, a lead connector 479-1 to 579-N may be provided with a DC blocking stimulation capacitor ($C_{DC}$) for facilitating direct current flow blocking functionality with respect to the corresponding electrode that may be configured to operate as a stimulation node in accordance with a pulse definition of a selected program record. Although some of the electrodes may also be configured to operate as sensing nodes in addition to providing stimulation (e.g., having an AC-coupling sense capacitor ($C_{SENSE}$) in addition to the DC blocking stimulation capacitor), such arrangements are not shown herein without loss of generality. By way of illustration, DC blocking stimulation capacitor $C_{DC-1}$ 472-1 is coupled to lead connector 479-1. Likewise, remaining lead connectors 479-N may be provided with respective $C_{DC-N}$ 472-N to facilitate DC blocking with respect to each corresponding lead electrode thereof.

In some arrangements, driver interface block 460 may include appropriate multiplexing and selection circuitry 462 and anode/cathode/inactive electrode selection circuitry 464 for therapy, measurement and sensing/diagnostics purposes wherein different electrodes of an electrode grouping of the lead system may be selectively configured for stimulation (e.g., anodic or cathodic stimulation), sensing, or designating unused/inactive states, etc., with appropriate electrical connections being made within an IPG device accordingly relative to the various components therein. In some embodiments, portions of diagnostic circuitry 458 may comprise suitable analog-to-digital converter (ADC) circuitry configured for digital voltage and/or impedance measurement and associated signal processing using known techniques. In some arrangements, measurement circuitry can be external and/or internal, on-board or off-board, and/or may be coupled to other measurement devices, wherein the circuitry may be (re)configured depending on the selected program record type and/or the measurement mode indicia indicated therein. Still further, a stimulation engine (SE) selection block, module or logic 466 may be provided for selectively coupling a (sub)set or portion of lead connectors to a select SE, where multiple SEs are provided in some example embodiments, under programmatic control that may be mediated via an authorized therapy application executing on an external programmer (e.g., a clinician programmer or a patient controller) as previously noted.

FIGS. 5A-5J illustrate example electrical stimulation leads having one or more electrodes that may be energized using waveform generation according to an embodiment of the present patent disclosure. One or more stimulation leads 500A to 500J are exemplary of a variety of commercially available leads, such as deep brain leads, percutaneous leads, paddle leads, etc., as shown in FIGS. 5A-5J, respectively, wherein conductive electrodes can be planar electrodes, ring electrodes, segmented or split electrodes, etc., commonly shown as electrodes 502. The non-conducting portions of leads 500A-500J may comprise one or more insulative materials and/or biocompatible materials to allow the lead to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

An example lead having electrodes 502 may be implanted in a patient such that one or more stimulation electrodes 502 of each stimulation lead 500A-J are positioned or disposed near, adjacent to, directly on or onto, proximate to, directly in or into or within the target tissue or predetermined site of the patient. Techniques for implanting stimulation electrodes are well known by those of skill in the art and may be positioned in various body tissues and in contact with various tissue layers; for example, deep brain, cortical, subdural, subarachnoid, epidural, cutaneous, transcutaneous and subcutaneous implantation is employed in some embodiments.

By way of illustration, set forth below are exemplary tissues, regions and/or organs that may be stimulated and/or diagnostically monitored under waveform program playback in some embodiments:

A) Brain:

Central neuronal tissue includes brain tissue, spinal tissue or brainstem tissue. Brain tissue can include the frontal lobe, the occipital lobe, the parietal lobe, the temporal lobe, the cerebellum, or the brain stem. More specifically, brain tissue can include subcortical targets, for example, thalamus/subthalamus (i.e., thalamic nuclei, medial and lateral *geniculate* body, intralaminar nuclei, nucleus reticularis, pulvinar, subthalamic nuclei (STN), etc.), basal ganglia (i.e., putamen, caudate nucleus, globus pallidus), hippocampus, amygdala, hypothalamus, epithalamus, mammillary bodies, ventral tegmental area (VTA), substantia nigra, corpus callosum, fornix, internal capsula, anterior and posterior commissural, cerebral peduncles etc. Brain tissue also includes cerebellum, cerebellar peduncles, and cerebellar nuclei such as fastigial nucleus, globose nucleus, dentate nucleus, emboliform nucleus. Still further, in addition to the above mentioned subcortical targets, brain tissue also includes cortical targets, for example, auditory cortex, prefrontal cortex, the dorsolateral prefrontal cortex, the ventromedial prefrontal cortex, the cingulate cortex, subcallosal area, anterior cingulate cortex, the subgenual anterior cingulate cortex, the motor cortex and the somatosensory cortex. The somatosensory cortex comprises the primary, the secondary somatosensory cortex, and the somatosensory association complex. Still further, the somatosensory cortex also includes Brodmann areas 1, 2, 3, 5, and 7. Yet further, brain tissue can include various Brodmann areas for example, but not limited to Brodmann area 9, Brodmann area 10, Brodmann area 24, Brodmann area 25, Brodmann area 32, Brodmann area 39, Brodmann area 41, Brodmann area 42, and Brodmann area 46.

While not being bound by the description of a particular procedure, patients who are to have an electrical stimulation lead or electrode implanted into the brain for deep brain stimulation, generally, first have a stereotactic head frame, such as the Leksell, CRW, or Compass, mounted to the patient's skull by fixed screws. Subsequent to the mounting of the frame, the patient typically undergoes a series of magnetic resonance imaging (MRI) sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. In some embodiments, a current way to do this is to rigidly mount the head frame to the surgical table. Subsequently, a series of reference points (e.g., fiducials) may be established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECT scan, fMRI, MSI), or indirectly using interactive anatomical atlas programs that map the atlas image onto the stereotactic image of the brain. In some arrangements, the anatomical target(s) or predetermined site(s) may be stimulated directly or affected through stimulation in another region of the brain.

In addition to deep brain stimulation, cortical stimulation can also be used to stimulate various brain tissues. Any of the stimulation leads illustrated in FIGS. 5A-5J can be used for cortical stimulation, as well as any other cortical electrode or electrode array. For implanting conventional cortical electrodes, it typically requires a craniotomy under general anesthesia to remove a relatively large (e.g., thumbnail-sized or larger) window in the skull. A pilot hole (e.g., 4 mm or smaller) can be formed through at least part of the thickness of the patient's skull adjacent a selected or predetermined site. In certain embodiments, the pilot hole can be used as a monitoring site.

The location of the pilot hole (and, ultimately the electrode received therein) can be selected in a variety of fashions, for example, the physician may use anatomical landmarks, e.g., cranial landmarks such as the bregma or the sagittal suture, to guide placement and orientation of the pilot hole or the physician may use a surgical navigation system. Navigation systems may employ real-time imaging and/or proximity detection to guide a physician in placing the pilot hole and in placing the electrode in the pilot hole. In some systems, fiducials are positioned on the patient's scalp or skull prior to imaging and those fiducials are used as reference points in subsequent implantation. In other systems, real-time MRI or the like may be employed instead of or in conjunction with such fiducials. A number of suitable navigation systems are commercially available, as is known to one skilled in the art. Once the pilot hole is formed, the threaded stimulation lead may be advanced along the pilot hole until the contact surface electrically contacts a desired portion of the patient's brain. If the stimulation lead is intended to be positioned epidurally, this may comprise relatively atraumatically contacting the dura mater; if the electrode is to contact a site on the cerebral cortex, the electrode will be advanced to extend through the dura mater. Thus, the lead may be placed epidurally or subdurally for cortical stimulation in some therapy systems having waveform program generation, storage and playback.

B) Spinal Cord and/or Peripheral Nerves

Peripheral nerves can include, but are not limited to olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, occipital nerve (e.g., suboccipital nerve, the greater occipital nerve, the lesser occipital nerve), the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves. Furthermore, peripheral neuronal tissue can include but is not limited to peripheral nervous tissue associated with a dermatome.

Spinal tissue can include the ascending and descending tracts of the spinal cord, more specifically, the ascending tracts of that comprise intralaminar neurons or the dorsal column. For example, the spinal tissue can include neuronal tissue associated with any of the cervical vertebral segments (C1, C2, C3, C4, C5, C6, C7 and C8) and/or any tissue associated with any of the thoracic vertebral segments (T1, T2, T3, T4, T5, T6, T7, T8, T9, T10, T11, T12) and/or any tissue associated with any of the lumbar vertebral segments (L1, L2, L3, L4. L5, L6) and/or any tissue associated with the sacral vertebral segments (S1, S2, S3, S4, S5). More specifically, the spinal tissue is the dorsal column of the spinal cord. The brainstem tissue can include the medulla oblongata, pons or mesencephalon, more particular the posterior pons or posterior mesencephalon, Lushka's foramen, and ventrolateral part of the medulla oblongata.

In other embodiments, the stimulation leads may be positioned in communication with the neuronal tissue of the spinal cord, more specifically, the dorsal column of the spinal cord. For example, stimulation electrodes are commonly positioned external to the dura layer surrounding the spinal cord. Stimulation on the surface of the cord is also contemplated, for example, stimulation may be applied to the spinal cord tissue as well as to the nerve root entry zone. Stimulation electrodes may be positioned in various body tissues and in contact with various tissue layers; for example, subdural, subarachnoid, epidural, and cutaneous, and/or subcutaneous implantation is employed in some embodiments.

Spinal cord stimulation, e.g., by way of program record playback by a waveform player as set forth herein, can be accomplished utilizing either percutaneous leads and/or laminotomy type leads that comprise a paddle. Percutaneous leads commonly have two or more equally-spaced electrodes which are placed above the dura layer through the use of a Touhy-like needle. For insertion, the Touhy-like needle is passed through the skin between desired vertebrae to open above the dura layer.

In contrast to the percutaneous leads, laminotomy leads have a paddle configuration and typically possess a plurality of electrodes (for example, two, four, eight, sixteen or twenty) arranged in one or more columns. Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place that tends to migrate less in the operating environment of the human body. Depending on the position of insertion, however, access to the dura may only require a partial removal of the ligamentum flavum at the insertion site. In some embodiments, two or more laminotomy leads may be positioned within the epidural space, and the leads may assume any relative position to one another.

In certain embodiments, the stimulation leads may be placed subcutaneously on the patient's head. For example, one or more stimulation leads can be implanted subcutaneously such that one or more stimulation electrodes are positioned in communication with a dermatome area, for example (C1, C2, C3, C4, C5, C6, C7, and C8), cervical nerve roots (e.g., C1, C2, C3, C4, C5, C6, C7 and C8) cranial nerves (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve) and/or occipital area. For example, one or more stimulation electrodes are positioned in the C2 dermatome area/C3 dermatome area, subcutaneously, but superior to the galea. Within certain areas of the C2 dermatome area or occipital or occiput area, there is little or no muscle, this area primarily consists of fat, fascia, periosteum, and neurovascular structures (e.g., galea). More specifically, the electrode can be implanted in a subcutaneous fashion such that the electrode is positioned below the skin, above the bone on the back of the head or superior to the periosteum. On the back of the head, the probe is positioned in the C2 dermatome area or positioned at the back of the patient's head at about the level of the ear.

C) Brainstem Stimulation

Implantation of a stimulation lead in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead on, in, or near the brainstem may be positioned around the head. Another alternative technique can include, a modified midline or retrosigmoid posterior fossa technique.

In certain embodiments, electrical stimulation lead is located at least partially within or below the dura mater adjacent the brainstem. Alternatively, a stimulation lead can be placed in communication with the predetermined brainstem area by threading the stimulation lead up the spinal cord column, as described above, which is incorporated herein.

Still further, a predetermined brainstem area can be indirectly stimulated by implanting a stimulation lead in communication with a cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve indirectly stimulates the predetermined brainstem tissue. Such techniques are further described in U.S. Pat. Nos. 6,721,603; 6,622,047; and 5,335,657, each of which is incorporated herein by reference.

Figure 6:
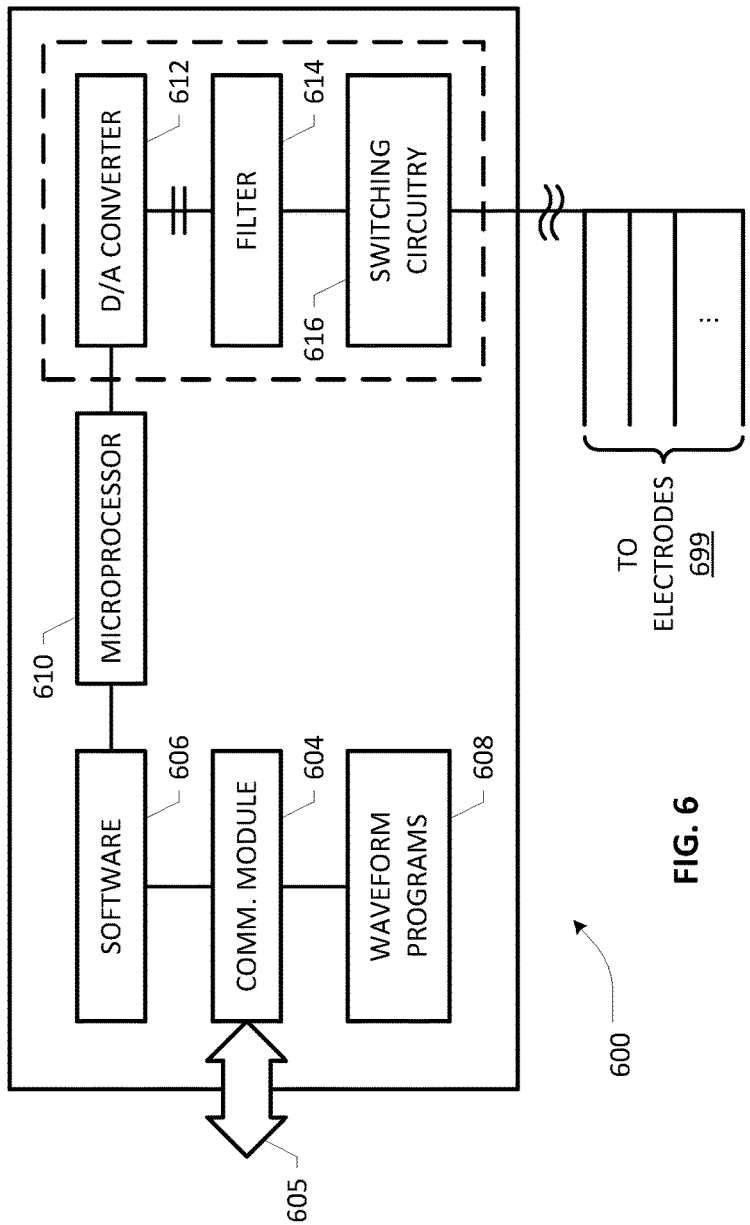
FIG. 6 depicts a block diagram of an IMD having a programmable stimulation engine and associated communication module in one arrangement for storing and playback of program records according to an embodiment of the present patent disclosure.

FIG. 6 depicts a block diagram of a system including an IMD having a programmable stimulation engine and associated communication module in one arrangement for storing and playback of program records according to an embodiment of the present patent disclosure. It will be apparent to skilled artisans that various functionalities associated with example blocks shown as part of IMD 602 of system 600 may be distributed and/or integrated among one or more blocks, subsystems and/or modules described hereinabove with respect to IMD 302 of FIG. 3 and/or other drawing Figures set forth herein. A communication module or processor 604 is operative with a communication channel 605 for communicating with an external device or programmer (not shown in this FIG.) for, inter alia, receiving waveforms or program records therefrom, either dynamically or as files (i.e., in a static manner) as previously noted. At least a portion of software/firmware 606 and associated processor 610 may comprise a controller or stimulator engine operative to actuate a driver portion 618 for causing stimulation from a selected program record pre-specified by the external programmer. As defined elsewhere in the present patent disclosure, a "program record" is a file which, when loaded into an active buffer region associated with processor 610, is operative to generate a pre-specified stimulation pattern. Accordingly, for purposes of some example embodiments herein, stimulation is driven from pre-specified program records identified, supplied, or otherwise provided by the external device, wherein each program record contain separate definitions of pulse characteristics and timing intervals. In some example embodiments, a program record may be played until completion or may continue to be played in a loop depending on the information provided in the program record. As will be seen further below, this concept may be referred to as a "waveform player", which may be configured to apply stimulation intended to provide the flexibility and versatility required to support existing as well as future stimulation needs in a therapy application scenario while providing a low power solution to stimulation.

In some implementations, various signal parameters identified in and/or associated with a program record may be loaded into software/memory 606, whereby the desired wave pattern or signals are generated using processor/microcontroller 610. In some implementations, a standard digital-to-analog converter (DAC) 612 of the driver portion 618 may receive the calculated digital signals and generate analog output pulses corresponding to the values of the digital signals. The generated output pulses may be propagated from IMD 602 through an output capacitor arrangement. Optionally, any suitable filter 614 can be used to smooth or shape the signals. In some implementations, smoothed, unsmoothed or unfiltered signals can be transmitted to switching circuitry 616 which provides the signals to select electrodes disposed in one or more leads 699, thereby stimulating the neuronal tissue using the pulse and timing interval definitions of the program record.

In one arrangement, different patterns of pulse definitions and timing interval definitions may be generated using and/or supplemented with signal sampling and processing techniques to inject various sequences of irregularity in a program record in order to avoid and/or mitigate the effect of tissue habituation. For example, a sampling procedure may involve using a $1/f^\beta$ noise signal such as pink noise, red or brown noise or black noise to optimize or vary the stimulation parameters. In a related variation, the generated $1/f^\beta$ noise signal may be filtered, combined, or otherwise processed, for example, whereby the generated $1/f^\beta$ noise is utilized as a background signal noise over another signal with a spectral peak at a selected frequency. For example, an alpha peak, beta peak, delta peak and/or theta peak can be added to the $1/f^\beta$ noise. The peaks can be generated using typical known frequencies or the peaks can be individualized for each patient. Yet further, the $1/f^\beta$ noise can be combined with standard tonic and/or burst stimulation patterns for provisioning in a program record as part of its pulse definition set and/or timing interval definition set to further enhance the optimization or prevent habituation. In still further arrangements, a stimulation system may involve measuring or detecting given neuronal signals (e.g., brain signals) that can be used to modulate pulse definitions used in generating program records. With sense electrodes disposed near, adjacent to, directly next to or within the target neuronal tissue, for example, brain tissue, some representative embodiments may be configured to utilize the detection and analysis of neuronal activity, such as electroencephalography (EEG) measurements, which may be processed using available signal processing techniques executed on a computing platform or device (e.g., time domain segmentation, fast Fourier transform (FFT) processing, windowing, logarithmic transforms, etc.). Additional details regarding the use of $1/f^\beta$ noise signals and sensed biological signals in generating stimulation may be found in U.S. Patent Application Publ. No. 2018/0304083, entitled "USE OF A NEW STIMULATION DESIGN TO TREAT NEUROLOGICAL DISORDERS", which is incorporated by reference herein. In still further arrangements, signal sampling and processing techniques to provide waveforms based on arbitrary or defined signals as set forth in U.S. Pat. No. 7,715,912, entitled "SYSTEM AND METHOD FOR PROVIDING A WAVEFORM FOR STIMULATING BIOLOGICAL TISSUE", incorporated by reference herein, may also be used in conjunction with an example embodiment of the present patent disclosure in additional or alterative variations.

Figure 7:
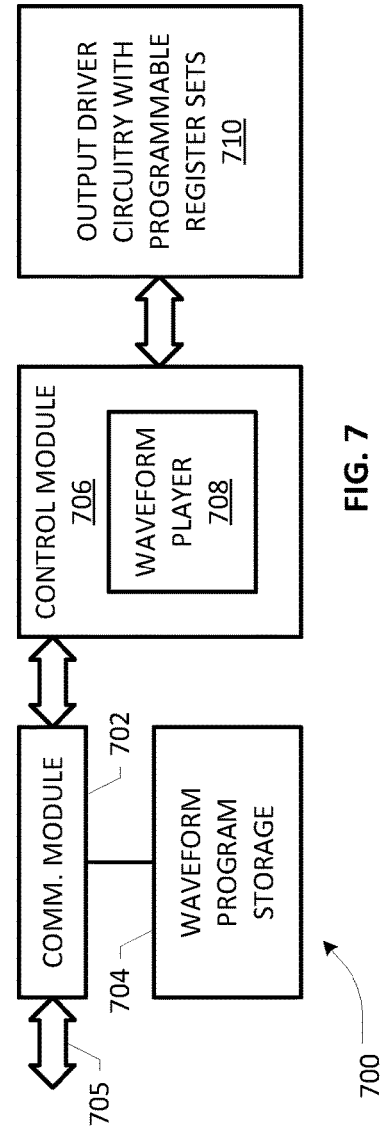
FIG. 7 depicts a block diagram of an IMD in another arrangement for storing and playback of program records according to an embodiment of the present patent disclosure.

FIG. 7 depicts a block diagram of an IMD in another representation configured for storing and playback of program records according to an embodiment of the present patent disclosure, wherein at least a portion of the foregoing functionalities and structural components of FIG. 6 are rearranged in a further variation. Similar to the description set forth above, a communication module 702 provided with IMD 700 is operative with a communication channel 705, e.g., a BLE channel, wherein appropriate embedded OS or firmware may be configured to download, receive or otherwise obtain one or several program records from an external device for storage in a memory 704. A control module 706 is provided with a waveform player 708 for playing a select program record copied from storage 704 into a program buffer (not shown in this FIG.) associated with waveform player 708. As will be set forth below, communication module 702 may be provided with a program record manager for facilitating the transfer of a select program record under control of a therapy application executing on the external device. An output driver circuitry block 710 may be provided with a number of programmable register sets that may be optimized in a manner to facilitate a larger number of pulse set definitions to be applied to select electrodes according some embodiments herein. Additional details with respect to the foregoing functionalities and structural components are set forth immediately below taking reference to the remaining drawing Figures of the present patent disclosure.

Figure 8:
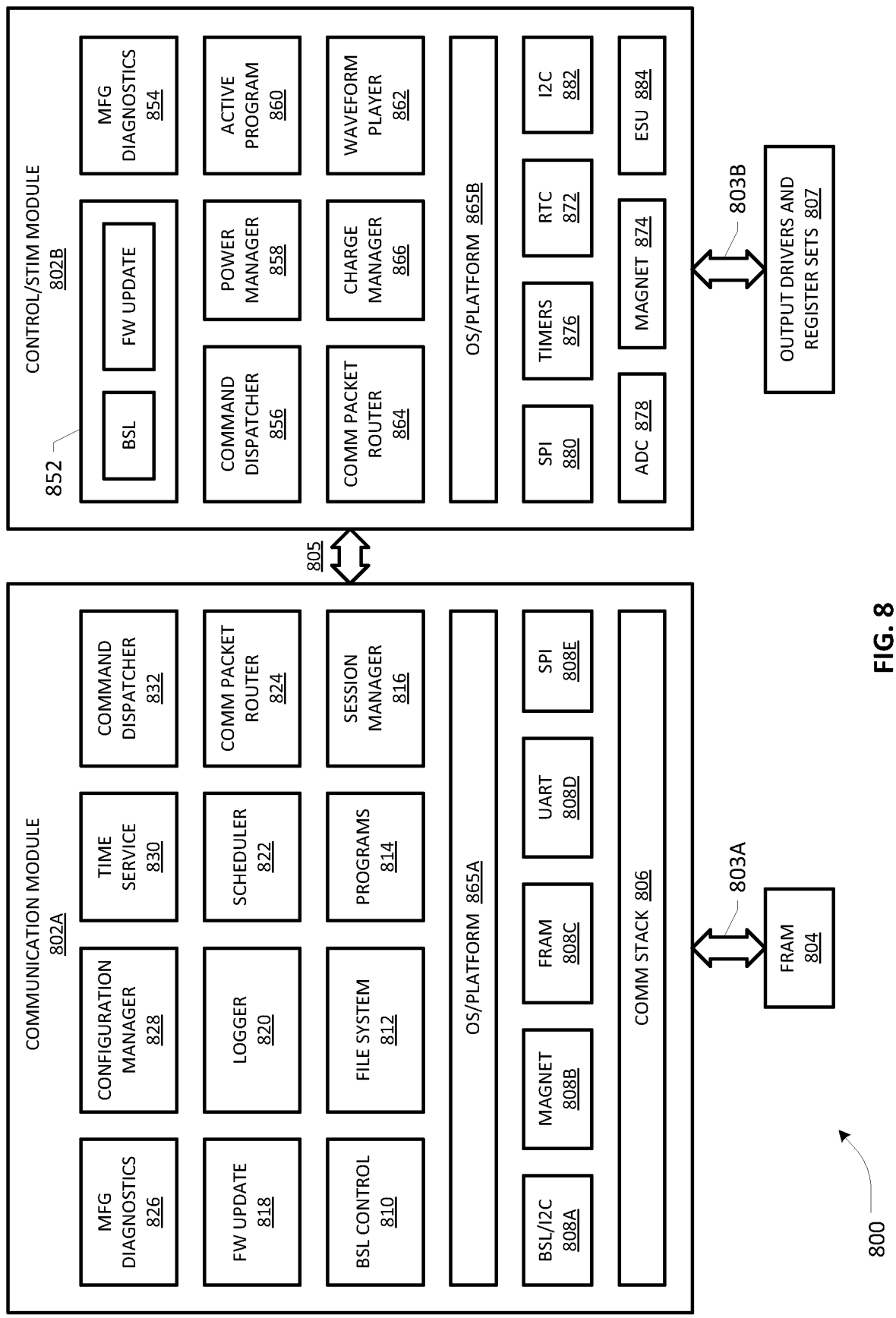
FIG. 8 depicts a block diagram illustrating further details of the IMD arrangement shown in FIG. 7 according to an embodiment of the present patent disclosure.

FIG. 8 depicts a block diagram of an IMD 800 that illustrates further details of the IMD arrangement shown in FIG. 7 according to an embodiment of the present patent disclosure. Broadly, a communication module 802A and a control/stimulation module 802B may be implemented based on respective processors/microcontrollers, e.g., a first module and a second module, with each processor/microcontroller configured with or configured to cooperate with suitable software/firmware/OS modules that may be primarily dedicated to either communications management or control and stimulation management, respectively. Further, to effectuate waveform-based stimulation functionality of IMD 800, two separate pieces of circuitry/hardware are respectively coupled to communication module 802A and control module 802B via respective interfaces, e.g., serial peripheral interface (SPI) 803A and SPI 803B. As illustrated, communication module 802A is interfaced via SPI 803A with a persistent storage device 804, e.g., a nonvolatile Ferro-electric Random Access Memory or FRAM device, wherein the storage device 804 is operative to store a plurality of program records received from an authorized external device or a medical/healthcare provider network node. Control module 802B is interfaced via SPI 803B with an output driver circuit 807 operative to generate or drive stimulation pulses to select electrodes depending on a select program record. Each module 802A, 802B may be operative with a suitable Real-time OS (RTOS) 865A, 865B, respectively, for providing a software platform configured to support respective software/firmware modules for effectuating respective functionalities.

A communication stack 806 of communication module 802A may be configured to interface with a BLE antenna (not shown) for effectuating M2M communications with an external device and/or other network entities, e.g., for receiving, downloading or otherwise obtaining therapy instructions as well as program records that may have been generated by the external device as described previously. In one arrangement, an example BLE communication protocol for communication with IMD 800 may be provided as a two-layer protocol, wherein the outer layer is configured for packet routing and the inner layer is configured for control. In one arrangement, the BLE channel may be treated as a physical layer with regards to sending/receiving information to and from IMD 800, wherein data integrity may be handled according to known BLE standards, e.g., BLE 5.0 standard.

Within the context of BLE, application data may be uniquely identified as attributes, which are transferred by the Attribute Protocol (ATT) based on a Generic Attribute (GATT) Profile, which may include GATT functionality such as a Write Request, Write Response, Notification, etc. Further, over-the-air (OTA) application firmware (FW) updates may be provided to IMD 800 via secure BLE, wherein the downloaded images may be required to be digitally signed and be verified as being initiated by a secure authenticated therapy application.

In addition to BLE, various communication interface modules may be provided as part of communication module 800A: bootstrap or boot loader (BSL) and inter-integrated circuit (I²C) manager or module 808A, magnet communications interface manager or module 808B, FRAM interface manager or module 808C, Universal Asynchronous Receiver/Transmitter (UART) manager or module 808D, and SPI manager or module 808E. In one arrangement, a plurality of functional/structural modules of communication module 802A may comprise the following: BSL control 810, file system 812, program record manager 814, session manager 816, FW update module 818, data logger 820, task/event scheduler 822, packet router 824, manufacturer diagnostics 828, configuration manager 828, time service module 830, and command dispatcher module 832. As will be seen below, program record manager 814 may be configured to utilize at least some aspects of one or more of the foregoing modules to effectuate a program record transfer from FRAM storage 804 to control module 802B via a suitable inter-module communication interface 805 under therapy application control for playback (i.e., stimulation).

In one arrangement, interface 805 may be representative of one or several interface types for effectuating different types of communications between modules 802A and 802B, e.g., including data and signaling/control communications. For example, inter-module reset communications, BSL/I²C communications, SPI communications, etc. may be effectuated between communication module 802A and control module 802B. Similar to RTOS 865A of communication module 802, RTOS 865B of control module 802B may be configured to support a plurality of functional/structural modules operative to effectuate the overall control and management of waveform-based stimulation in conjunction with output driver circuitry block 807. In one arrangement, control module 802B may therefore include, without limitation, the following: BSL/FW update module 852, manufacturer diagnostics 854, command dispatcher module 856, power manager 858, active program module 860, waveform player 862, charge manager 866, and packet router 864. Further, various communication interface modules may be provided as part of control module 800B: SPI manager or module 880, I²C manager or module 882, and magnet communications interface manager or module 874. Control module 802B also includes various hardware components such as, e.g., timers 876, ND converters 878, real-time clock (RTC) 872 as well as mode detector 884. In one arrangement, waveform player 862 may be configured as a driver to output driver circuitry 807 operative under control of firmware based on a select program record provided to the active program module 860, wherein appropriate stimulation may be provided by output driver circuitry 807 to select electrodes according the pulse definitions in the program record. Output driver circuitry 807 may be provided with a leads interface (not specifically shown in this FIG.) that may be configured as a lead-agnostic interface regardless of which specific electrodes are selected for use. In one arrangement, characteristics such as contact surface area and lead impedance due to length and materials may be accounted for and handled at application software level.

In one arrangement, magnet communication interface(s) 8086/874 may be utilized in a scenario wherein a magnet may be used as an additional/alternative control or triggering device based on sensing a magnetic field such that different modes may be accomplished by detecting magnetic events of varying encoded durations. For example, the magnet may be brought within the proximity or vicinity of IMD 800 for a particular time duration (e.g., a number of seconds) and then removed. The duration and state of the device may then used to interpret this event as a specific action. Depending on implementation, magnet interface(s) may be configured to provide one or more of the following functionalities: alternative method of ON/OFF control of stimulation; acknowledgement of physical presence for security challenges required by operations such as bonding and firmware download; and restore/disable BLE communications. Additional details regarding the initiation and control of a bi-directional communication link between two devices using a proximate triggering device may be found in U.S. Pat. No. 9,288,614, entitled "SYSTEMS AND METHODS FOR INITIATING A COMMUNICATION LINK BETWEEN AN IMPLANTABLE MEDICAL DEVICE AND AN EXTERNAL DEVICE", which is incorporated by reference herein.

Functionally, data may be transmitted/received over BLE or UART interfaces of communication module 802A, which may be processed by a routing protocol executed by packet router 824 for determining the destination and delivering the packets to the appropriate endpoint for further processing (e.g., in association with command dispatcher 832). Inter-processor or inter-module communications may be effectuated over SPI as previously noted. Configuration manager 828 is responsible for transitioning between IMD states including, e.g., firmware updates, surgery mode, magnetic resonance imaging (MRI) mode, therapy mode, and diagnostics mode. Depending on implementation, such transitions may cause playback of a select program record or a default program record by waveform player 862.

In one arrangement, file system module 812 is operative to provide access and data management of persistent data stored on FRAM 804, which may be partitioned into multiple virtual drives to maintain control of resource allocation, wherein the entire storage space may be treated as a virtual disk drive. A fixed number of bytes may be allocated to each partition such that when a partition reaches capacity it may not be allowed to consume additional space from other partitions. In one arrangement, provisioning of the file system provides individual partitions for diagnostic files, program records and space allocated for use by the therapy/remote application.

In one arrangement, programs manager or program records manager 814 is responsible for maintaining and managing the program records stored on FRAM 804 according to file system module 812. In one arrangement, select programs or program records may be loaded from the data store (e.g., FRAM 804) to the active program area in control module 860 through the operation of program records manager/module 814. Further, program records manager/module 814 is operative to facilitate saving and/or downloading of programs to the data store in addition to performing operations such as delete, copy, and read of stimulation program records.

Figure 9:
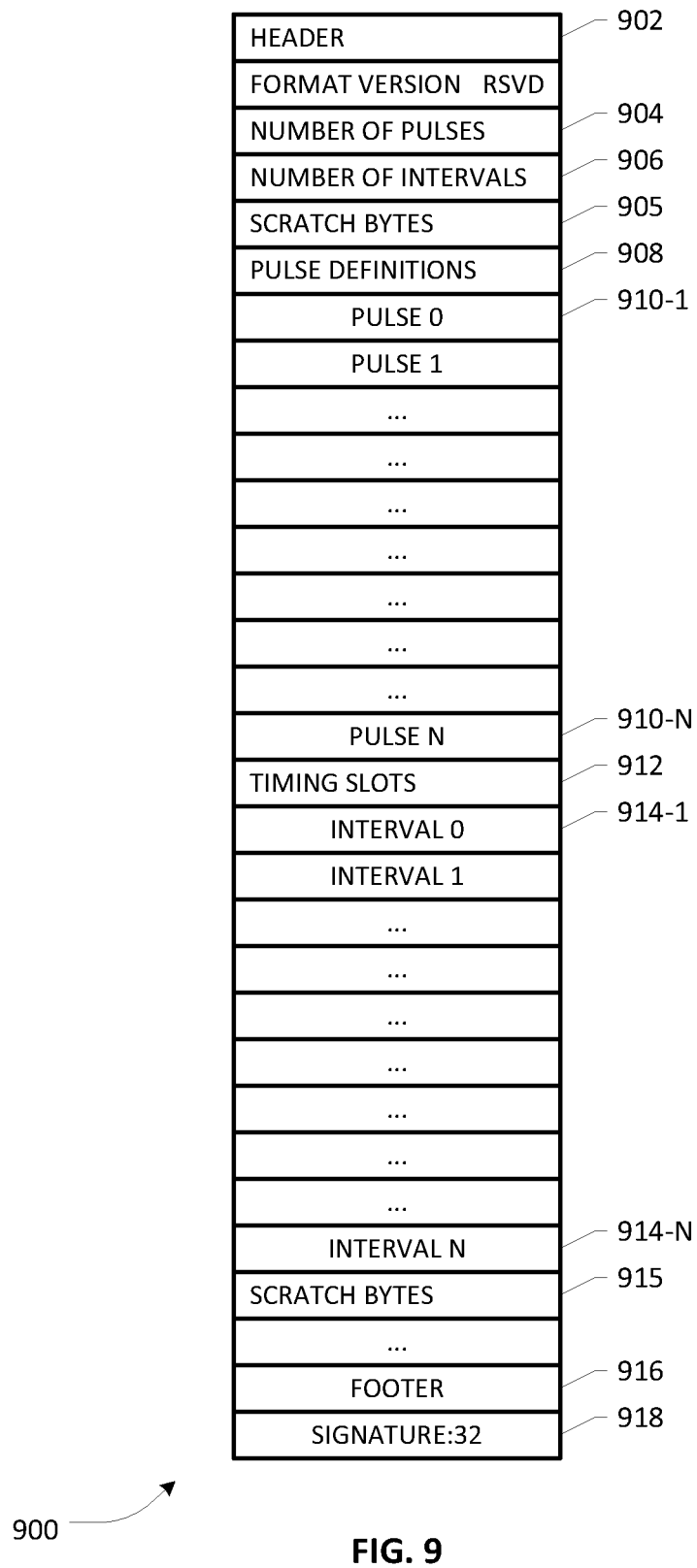
FIG. 9 depicts an example program record and associated format including multiple pulse definitions and time interval definitions for use by a waveform player for energizing a select set of electrodes according to an embodiment of the present patent disclosure.

FIG. 9 depicts an example program record and associated format including variable pulse definitions and time intervals for use by a waveform player for energizing a select set of electrodes according to an embodiment of the present patent disclosure. In one arrangement, a program or program record 900 comprises a header 902 which identifies the version of the program record, any global conditions to be used in playing the record, and the number of pulses and slot entries 904, 906, followed by the pulse definitions 908, interval/time slot definitions 912, meta-data storage, and then followed by a footer 916 and appended by a digital signature 918. A pulse definition is a set of pulse characteristics that may be applied by or during an interval. In one arrangement, an interval defines the time until the next pulse. In some arrangements, example program record format 900 may also optionally contain one or several scratch areas, which may comprise a certain amount of memory space set aside for any application data related to the program. By way of illustration, scratch areas 905 and 915 are exemplified in program record 900. In one arrangement, signature 918 is a digital signature operative to ensure data integrity with a Secure Hash Algorithm (SHA) hash such as, e.g., SHA256.

In one arrangement, each time a program record is loaded from FRAM 804 into the active program module 860, the signature is checked and the pulse and interval definitions are checked to verify that the selected program record meets minimum criteria for use as the active program by waveform player 862. In one arrangement, each interval indicates which pulse definition is to output in that time interval. In general, record sizes may be configured to be variable with up to a certain number of pulse definitions (e.g., pulse definitions 910-1 to 910-N) and a certain number of timing intervals (e.g., 914-1 to 914-N), each of which may be independently determined or applied in some embodiments.

In one arrangement, programs manager module 814 may be configured to provide support for overwriting default programming for certain types of modes, e.g., MRI mode, surgery mode and system impedance, as previously noted. For example, this may be accomplished through providing a process to specify a particular program record that will overwrite the system default method at initialization.

Turning to FIGS. 10A-10C, depicted therein are additional details relative to different portions of an example program record according to an embodiment of the present patent disclosure. By way of illustration, a record portion 1000A is further exemplary of a header portion of a program record such as record 900 described above, wherein an arbitrary-number-wide bit field (e.g., a 16-bit word) and having a predetermined depth may be allocated to carry various pieces of information as previously noted. In one arrangement, a format version 1004 and record type 1008 may be provided wherein a plurality of bits may be allocated to identify the mode of stimulation the program record is configured to execute when interpreted by a waveform player. As noted elsewhere in the present patent disclosure, record type 1008 may comprise modes such as "Therapy", "MRI", "Surgery Mode" and "System Impedance", etc. In a System Impedance mode, a program record comprises a diagnostic record that may be executed to perform runtime diagnostic impedance measurements during stimulation rather than performing such measurements offline (i.e., after a stimulation program has ended) as is done in some current IPG solutions. A bit field portion 1008 may be provided to identify stimulation clock frequencies (STCLKF) (e.g., in the range of a few hundreds of hertz to one or several thousands of hertz) as well as indicia to indicate whether any program settings are outside certain thresholds (Limit Exceeded or LXD). Certain indicators such as, e.g., program optimization indicator (OD), interval looping indicator (LD), magnet mode indicator (MA), may also be included in portion 1008 along with any unused bits (indicated as X). Separate bit fields 1010 and 1012 may be provided to indicate, identify or otherwise contain the number of pulses and the number of time intervals of the program record. A scratch bytes portion 1014 may comprise a plurality of bytes reserved for any application data related to the program as previously noted. In some arrangements, various optional indicators may be provided, e.g., dose on or dose off times 1016, 1018, stimulation shutoff delay 1020, etc.

An example pulse definition 1000B is illustrated in FIG. 10B, wherein a target pulse amplitude 1032, a maximum pulse amplitude 1034, current range 1036, and pulse width 1036 are shown in respective bit field portions or bytes. Additional information relating to pulse ramp/slope, discharge, interval index (e.g., the interval in which the pulse definition is to be applied), etc., are indicated in bit field portions 1040, 1042, 1044, along with other indicia including IPG can size, among others. A bit field portion 1046 is operative to indicate one or several electrodes (e.g., up to 16 electrodes in one arrangement) selected for applying stimulation according to the pulse definition. In one arrangement, each electrode requires two bits, thereby requiring a total of 32 bits for identifying and/or indicating a selection among 16 electrodes in an example implementation. Further, cathodic or anodic configuration of electrodes (as well as inactive electrode states where applicable) may also be appropriately indicated in the pulse definition 1000B. Depending on implementation, up to 64 pulse definition parameters may be configured involving characteristics such as, e.g., amplitude, polarity, pulse width, duty cycle, etc., in some arrangements.

An example time interval definition 1000C is illustrated in FIG. 10C, wherein an interval indicating a time duration until next pulse is provided in bit field portion 1052, which may be indicative of a duty cycle on a per time slot basis (e.g., in relation to a specified pulse width) in some embodiments and may range from a few microseconds to hundreds or thousands of microseconds or fractions or integers of milliseconds, or any other suitable time ranges. A pulse index (e.g., the pulse definition to be applied during the indicated interval) is shown in bit field portion 1054. Other indicia such as VMULT 1058, ADC 1960, repeat count 1062 and the number of records to repeat 1064 may also be provided in some arrangements. Still further, parameters such as voltage overhead pulse width error (OPE), voltage overhead active discharge error (ODE), falling edge of power start (PWE) and passive discharge fault (PDF), etc. may also be provided in additional and/or alternative variations.

It will be appreciated that a variety of pulse definition and interval definition combinations may be achieved by suitably cross-indexing within a program record in one arrangement. Accordingly, a large number of unique and complex waveforms can be implemented for providing stimulation within a single program record according to some embodiments.

Returning to FIG. 8, a select program record loaded into active program module 860 may be interpreted by waveform player 862 of IMD 800, as noted previously, wherein a select set of electrodes may be activated or otherwise energized for providing stimulation over a period of time according to the pulse definitions and time interval definitions therein, including, e.g., stimulation features such as cycle mode, inter alia. In general operation, active program module 860 may be configured to coordinate stimulation changes with waveform player 862 to provide seamless changes to pulse characteristics through an active program buffer. In one arrangement, an active program memory may be implemented as a 4K double-buffered program played by waveform player 862, which may also be referred to or configured to operate as the device driver for output driver circuitry 807 interfacing with the lead electrodes as previously noted. Skilled artisans will appreciate that double-buffering allows seamless transitions of program changes and provides a mechanism or process to make a group of program changes atomic, thereby creating the ability to support a transaction-based interface for updates to stimulation parameters.

In one arrangement, active program buffer/module 860 may be configured to contain the runtime version or copy of the designated program record, wherein the runtime image or code contains only the data required to drive stimulation. All data is represented in units relevant to their purpose/usage. Stimulation parameters, such as interval time and pulse width may be expressed in units of clocks. Amplitude may be represented in units of the programmed range of current (e.g., irange, where for a given irange, the least significant bit (lsb) may be determined as irange/255). In one arrangement, active program module 858 may be configured with code portions or pieces of software that may be pre-loaded at initialization by the program manager module when configured. Where configured with a default program, such code may comprise program instructions for certain modes, e.g., surgery mode and MRI mode. Whereas these programs may be prebuilt into active program module 860 by default, they can be overwritten by the program manager module in some implementations. When an appropriate ESU event is detected, surgery mode may be automatically activated, deactivating current stimulation. In one arrangement, MRI mode and surgery mode may be activated through a control protocol effectuated between communication module 802A and control module 802B of IMD 800.

Waveform player 862 drives the generation of stimulation through interpretation of stimulation records to the hardware of output driver circuitry 807 via SPI 803B, wherein appropriate FW/code portion(s) of waveform player 862 is responsible for the timing of a stimulation pulse and coordination of setting registers within output driver circuitry 807, which may be implemented as an ASIC in some embodiments. In one arrangement, the hardware of output driver circuitry 807 may include a predetermined number of register sets (e.g., 8 sets of registers, each set including a select number of registers, e.g., 2, 3, 4, 5, 6, or any other positive integer), which control the amplitude, pulse width, discharge mode, electrodes (e.g., up to 16 electrodes) and the polarity of a stimulation pulse, inter alia. Timing may be specified in counts of the system provided stimulation clock. Waveform player 862 may be configured to drive the interval timing of when each register drives a stimulation pulse onto the selected set of electrodes (from a total of 16 electrodes in one embodiment). The internal representation of the interval timing may be in stimulation clocks identified in a designated program record. Accordingly, conversion of time to clocks may take place when the stimulation program record is converted to a runtime version and loaded into the active program buffer.

In one arrangement, the register sets may be treated as a hardware (HW) cache to reduce the average cost (time and/or energy) of accessing stimulation pulse data. Further, the HW cache may be organized or optimized to extend the functional capabilities of the device beyond the limit of 8 sets. In one example embodiment, this may be implemented through a two-way set-associative cache algorithm or process wherein a memory address can be stored in any 2 lines of cache. For an 8-set register implementation, up to 16 pulse set definitions may be mapped in the two-way associative process using modulo-8 arithmetic in one implementation. Of the 8 register sets, a particular one may be selected by way of 3-bit digital control signal from waveform player 862.

Figure 11:
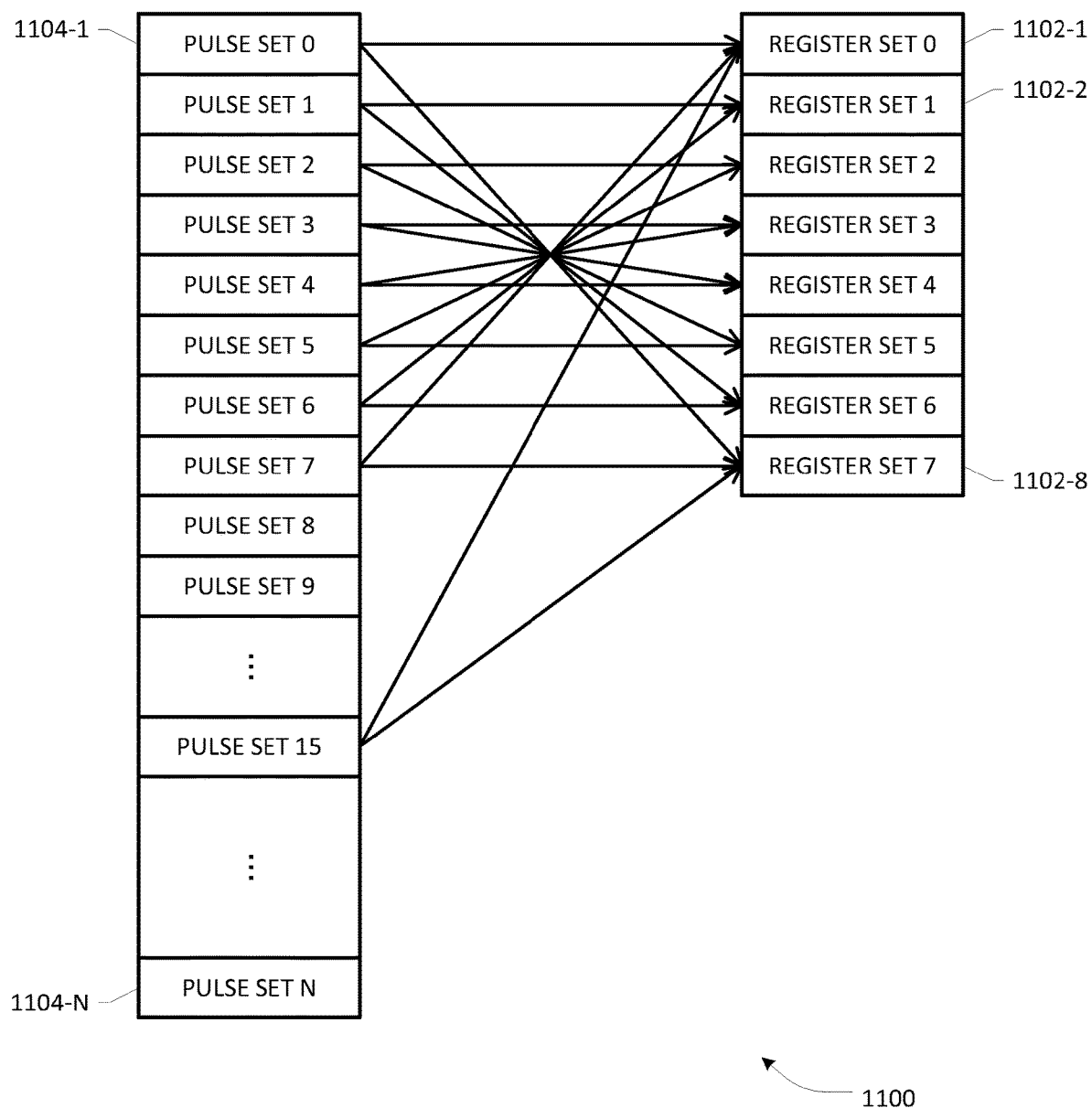
FIG. 11 depicts a two-way associative cache arrangement or process for mapping a plurality of pulse set definitions with a sub-plurality of register sets configured to drive one or more selected electrodes according to a program record interpreted by a waveform player of the present patent disclosure.

FIG. 11 depicts a two-way associative cache arrangement or process 1100 for mapping between a plurality of pulse set definitions and a sub-plurality of register sets configured to drive one or more selected electrodes according to a program record interpreted by a waveform player of the present patent disclosure. As illustrated, register sets 1102-1 to 1102-8 are associatively mapped with 16 pulse set definitions of a plurality of definitions 1104-1 to 1104-N. It will be appreciated that an associative cache implementation according to the teachings herein advantageously allows for a pulse definition that is actively output to be changed, which in turn allows the stimulation to be managed with a single Interrupt Service Routine (ISR), thereby conserving power in IMD 800. Processor power savings can be particularly significant in an implantable device especially where there is limited power supply. Further, extending the number of pulse definitions that can be supported by an IMD requires more registers to be written every pulse. Accordingly, to minimize the power and timing impacts, direct memory access (DMA) by way of HW cache implementation may be used as set forth herein for driving the transfer of data to output driver circuitry 807. It should be appreciated that two-way set-associative caching may be optimally implemented to allow for extension of the number of pulses while preventing additional power costs when the number of pulses is less than or equal to the number of HW register sets.

Figure 13:
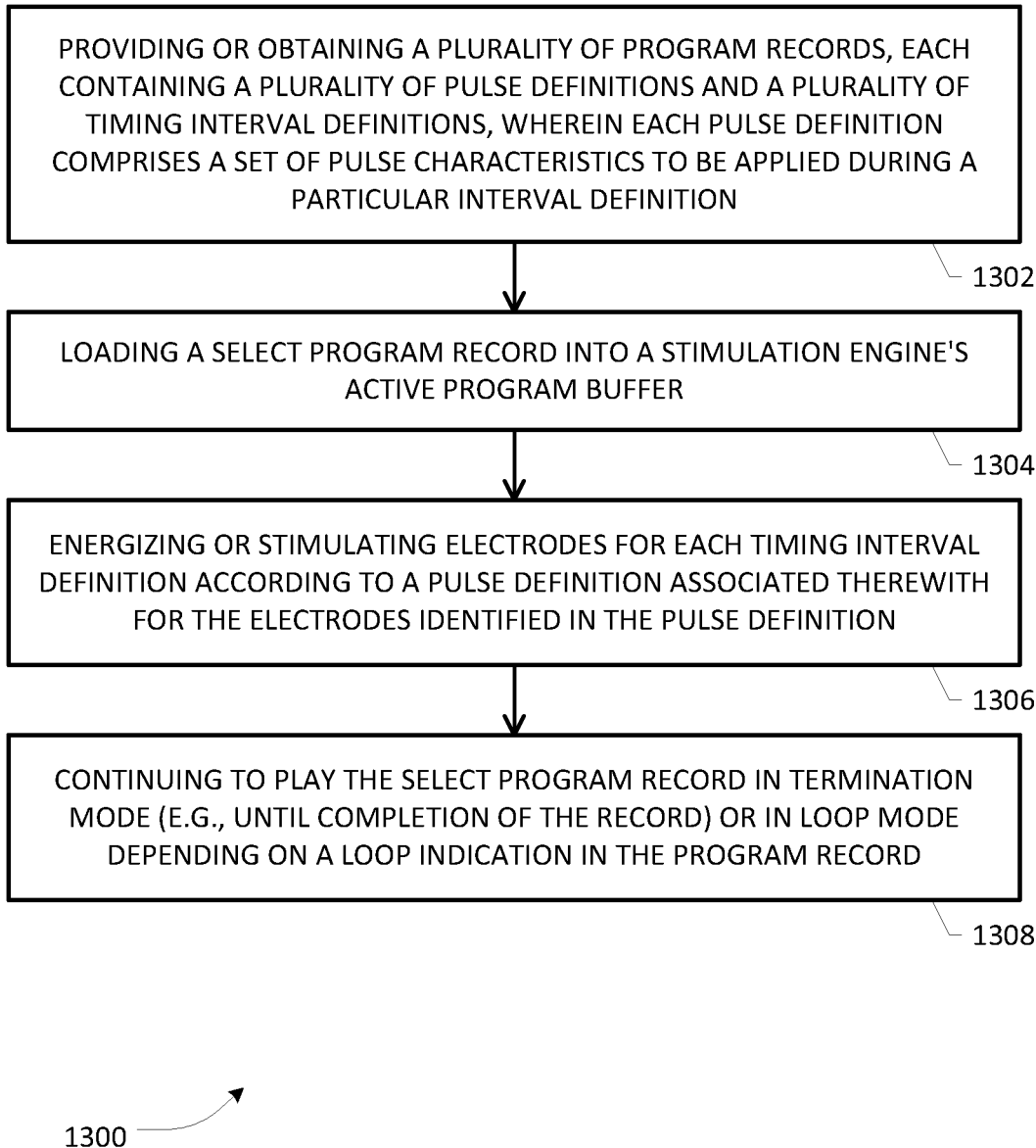
FIG. 13 is a flowchart of an example process according to an embodiment of the present patent disclosure.

FIG. 13 depicts a flowchart illustrative of blocks, steps and/or acts that may be (re)combined in one or more arrangements with or without additional flowcharts and/or message flow diagrams, if any, of the present patent disclosure for facilitating waveform-based stimulation according to some embodiments. At block 1302 of example process 1300, a plurality of program records may be obtained or received by an IMD, wherein each record is configured to contain a plurality of pulse definitions and a plurality of timing interval definitions. As set forth in detail above, each pulse definition comprises a set of pulse characteristics to be applied during a particular interval definition. At block 1304, a particular program record may be loaded into a stimulation engine's active program buffer, e.g., responsive to a command on the fly from a therapy application or due to pre-programmed control. At block 1306, a program record interpreter or waveform player is operative as a driver to interpret the data in the program record so as to generate suitable control/data signals to an output driver circuit for energizing or stimulating a select set of electrodes for each timing interval definition according to a pulse definition associated therewith for the electrodes identified in the pulse definition. At block 1308, process flow 1300 may continue to play the select program record (i.e., generate control/data signals to drive the output driver circuitry) until completion of the record (e.g., in termination mode) or in loop mode depending on a loop indication in the program record (e.g., over a given time duration).

Figure 12:
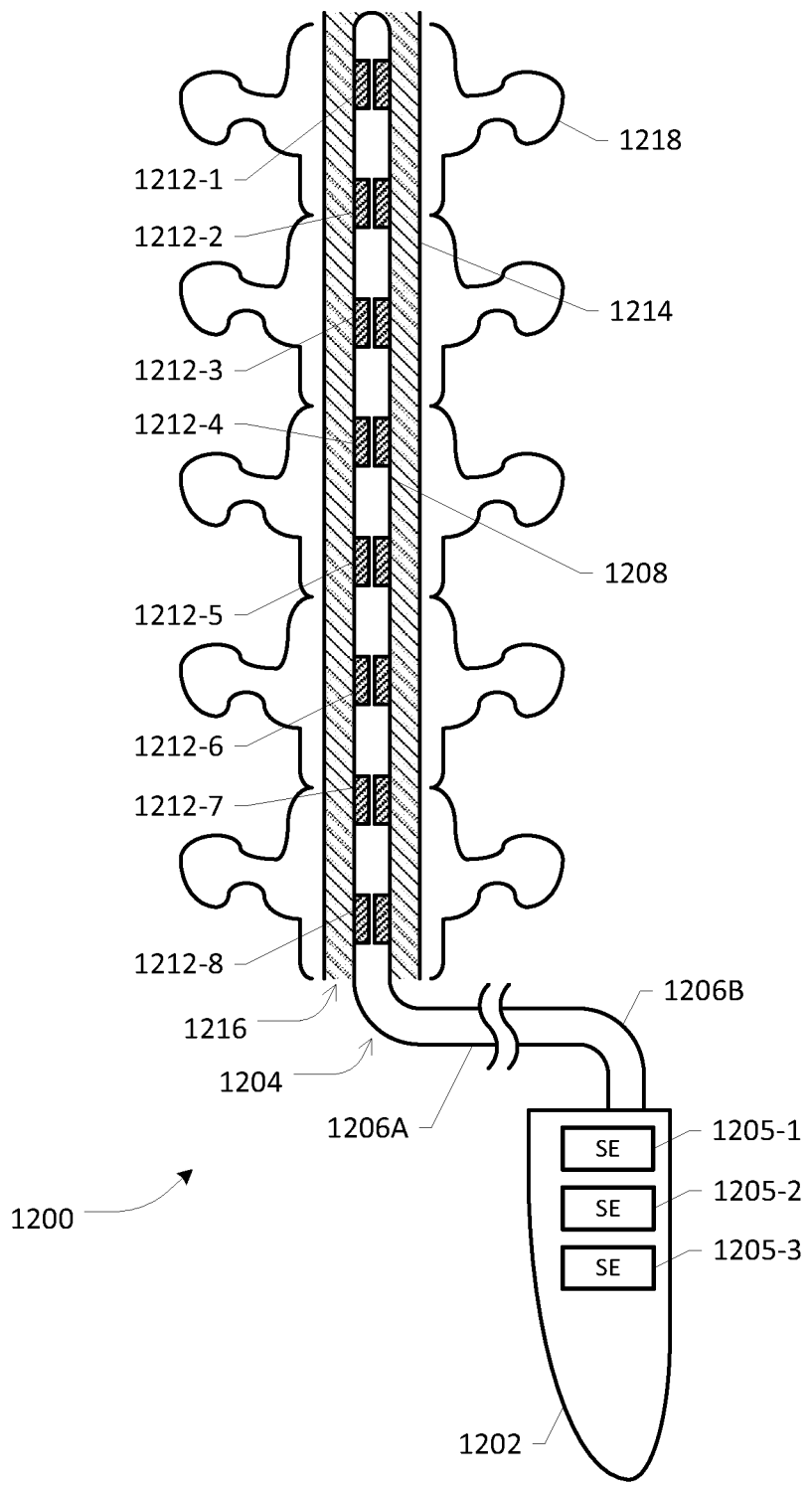
FIG. 12 illustrates an example spinal cord stimulation (SCS) therapy application involving an IMD with a programmable stimulation engine and associated lead system having a plurality of electrodes that may be stimulated using one or more program records according to an embodiment of the present disclosure.

FIG. 12 illustrates an example spinal cord stimulation (SCS) therapy application involving an IMD with a programmable stimulation engine and associated lead system having a plurality of electrodes that may be stimulated using one or more program records according to an embodiment of the present disclosure. As illustration, example SCS therapy system 1200 involves a pulse generator or IMD 1202 and associated lead system 1204 having a plurality of electrodes 1212-1 to 1212-8 wherein different groupings of electrodes may be simultaneously and independently energized pursuant to respective program records during a stimulation therapy according to an embodiment of the present patent disclosure. Preferably, lead system 1204 comprises a lead body 1206A/B coupled to an implantable lead 1208 that may be positioned at a desired target position in an epidural space 1216 defined by a plurality of vertebrae of a patient so as to be in close proximity to a nerve tissue of interest, e.g., spinal cord 1214. Example implantable lead 1208 includes eight electrodes 1212-1 to 1212-8, which may comprise ring electrodes, segmented or split electrodes, and the like that may be separated from one another by equal or unequal portions of encapsulating material. The implantable lead 1208 is connected via lead body 1206A/1206B to IPG/IMD 1202 that includes at least an embodiment of a stimulation engine (SE) module of the present patent disclosure (e.g., implemented as control module 802B shown in FIG. 8) that may be configured to be operative with suitable diagnostic circuitry, waveform player circuitry and associated output driver circuitry hardware. By way of example, three SEs 1205-1, 1205-2, 1205-3 are shown, which may be selectively and independently configured to provide different combinations of stimulation therapy to electrodes 1212-1 to 1212-8 using respective waveform player and output driver circuitry hardware. Illustratively, SE 1205-1 may be activated to stimulate electrodes 1212-1 to 1212-4 and SE 1205-2 may be activated stimulate electrodes 1212-5 to 1212-8, while SE 1205-3 may be inactive. Accordingly, electrodes 1212-1 to 1212-4 and electrodes 1212-5 to 1212-8 may be energized, i.e., stimulated, e.g., with appropriate constant current pulses, wherein the individual stimulation currents drawn via respective loads may be optimized based on respective SE control in some embodiments.

In the above-description of various embodiments of the present disclosure, it is to be understood that the terminology used herein is for the purpose of describing particular embodiments only and is not intended to be limiting of the invention. For example, although a constant current stimulation is particularly exemplified, the teachings herein maybe applied to a constant voltage stimulation system. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Also, some blocks in the flowcharts may be optionally omitted. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A stimulation therapy method using an implantable medical device (IMD), the IMD including a power supply and a lead system of one or more leads, wherein each lead includes a plurality of electrodes positioned proximate to a tissue of a patient, the method comprising:
   obtaining a plurality of program records from an external device, each program record including a plurality of pulse definitions and a plurality of time interval definitions, wherein a pulse definition comprises a set of pulse characteristics to be applied in a particular time interval, wherein each program record of the plurality of program records comprises an indicator indicating whether the program record is a therapy record for applying a stimulation therapy to the patient or a diagnostic record for performing a runtime impedance measurement with respect to the select set of electrodes;
   loading a runtime image of a particular program record into an active program buffer; and
   interpreting the runtime image to generate control signals to drive an output driver circuit for applying pulse characteristics to a select set of electrodes according to the pulse definitions of the particular program record.

2. The method as recited in claim 1, wherein each program record comprises a loop indicator indicating whether the program record is to be played in termination mode or loop mode, the method further comprising continuing to generate the control signals to drive the output driver circuit according to the particular program record in a loop mode based on the loop indicator indicating the program record is to be played in loop mode.

3. The method as recited in claim 1, wherein the set of pulse characteristics defined in a pulse definition comprises at least one of a target amplitude, a maximum amplitude, a current range, a pulse width, a discharge method, one or more indicia identifying the select set of electrodes, one or more indicia identifying whether a particular one of the select set of electrodes is operative as a cathode or an anode, and a time interval index.

4. The method as recited in claim 3, wherein the program record is further including an indicator identifying a number of pulses and an indicator identifying a number of time intervals.

5. The method as recited in claim 4, wherein each program record further comprises an indicator for identifying whether the program record is to be executed in a loop over a predetermined time period.

6. The method as recited in claim 4, wherein each time interval definition comprises a configurable time duration and a pulse index indicator identifying a specific pulse definition to be applied for the time duration.

7. The method as recited in claim 6, wherein the stimulation therapy applied by the particular program record comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

\* \* \* \* \*

UNITED STATES PATENT AND TRADEMARK OFFICE
CERTIFICATE OF CORRECTION

| | |
|---|---|
| PATENT NO. | : 12,364,867 B2 |
| APPLICATION NO. | : 17/501741 |
| DATED | : July 22, 2025 |
| INVENTOR(S) | : Robert Nobles et al. |

Page 1 of 1

It is certified that error appears in the above-identified patent and that said Letters Patent is hereby corrected as shown below:

In the Specification

Column 8, Line 10, delete "(1.11$s$)" and insert --(UIs)--;

Column 19, Line 40, delete "8086/874" and insert --808B/874--.

Signed and Sealed this
Ninth Day of September, 2025

Coke Morgan Stewart
*Acting Director of the United States Patent and Trademark Office*